US010352940B2

(12) United States Patent
Ahmad et al.

(10) Patent No.: US 10,352,940 B2
(45) Date of Patent: Jul. 16, 2019

(54) METHOD AND APPARATUS FOR ANALYZING ACETONE IN BREATH

(71) Applicant: Invoy Holdings, LLC, Aliso Viejo, CA (US)

(72) Inventors: Lubna M. Ahmad, Chandler, AZ (US); Brent C. Satterfield, Bountiful, UT (US); Rhett L. Martineau, Gilbert, AZ (US)

(73) Assignee: Invoy Holdings, LLC, Aliso Viejo, CA (US)

( * ) Notice: Subject to any disclaimer, the term of this patent is extended or adjusted under 35 U.S.C. 154(b) by 82 days.

(21) Appl. No.: 15/366,309

(22) Filed: Dec. 1, 2016

(65) Prior Publication Data
US 2017/0176447 A1    Jun. 22, 2017

Related U.S. Application Data

(63) Continuation of application No. 14/400,911, filed as application No. PCT/US2013/000135 on May 15, 2013, now Pat. No. 9,518,991.
(Continued)

(51) Int. Cl.
*G01N 21/00* (2006.01)
*G01N 33/64* (2006.01)
(Continued)

(52) U.S. Cl.
CPC ............ *G01N 33/64* (2013.01); *A61B 5/082* (2013.01); *A61B 5/097* (2013.01); *G01N 21/783* (2013.01);
(Continued)

(58) Field of Classification Search
CPC ........ G01N 21/00; G01N 33/64; G01N 33/50; G01N 33/48; A61B 5/082; A61B 5/08; A61B 5/00
(Continued)

(56) References Cited

U.S. PATENT DOCUMENTS 2,186,902 A    1/1940  Fortune
2,509,140 A    5/1950  Free
(Continued)

FOREIGN PATENT DOCUMENTS

EP    0279069       8/1988
EP    1 524 522     4/2005
(Continued)

OTHER PUBLICATIONS

Ahmad, L. et al., "Design of a Breath Ketone Sensor for Obesity Management", Poster Presentation, Fall Meeting of the Biomedical Engineering Society, 2004, in 3 pages.
(Continued)

*Primary Examiner* — Christine T Mui
(74) *Attorney, Agent, or Firm* — Knobbe, Martens, Olson & Bear, LLP

(57) ABSTRACT

Methods and devices are provided for analyzing acetone in breath. One such method comprises disposing a reactant in a reaction zone within the breath analysis device, wherein the reactant comprises a primary amine disposed on a surface, and wherein the reaction zone has an optical characteristic that is at a reference level. It also comprises pre-storing a liquid nitroprusside solution within the breath analysis device separately from the reactant. The method further comprises using the breath analysis device to cause the breath to contact the reactant in the reaction zone so that the acetone in the breath reacts with the reactant to form a reaction product and, after the reaction product has been formed, using the breath analysis device to cause the nitroprusside solution to contact and react with the reaction product and to facilitate a change in the optical characteristic of the reaction zone relative to the reference level. The method also comprises using the breath analysis device to detect the change in the optical characteristic to sense the
(Continued)

acetone in the breath. Apparatuses that use these methods are also described.

27 Claims, 36 Drawing Sheets

Related U.S. Application Data

(60) Provisional application No. 61/792,158, filed on Mar. 15, 2013, provisional application No. 61/646,924, filed on May 15, 2012.

(51) Int. Cl.
| | |
|---|---|
| *G01N 33/497* | (2006.01) |
| *A61B 5/08* | (2006.01) |
| *A61B 5/097* | (2006.01) |
| *G01N 21/78* | (2006.01) |
| *G01N 33/48* | (2006.01) |
| *A61B 5/00* | (2006.01) |
| *A61B 10/00* | (2006.01) |

(52) U.S. Cl.
CPC .......... *G01N 33/497* (2013.01); *A61B 5/0059* (2013.01); *A61B 2010/0087* (2013.01); *A61B 2560/0233* (2013.01); *G01N 2033/4975* (2013.01); *Y10T 436/202499* (2015.01)

(58) Field of Classification Search
USPC .................. 436/130; 356/433, 432
See application file for complete search history.

(56) References Cited

U.S. PATENT DOCUMENTS

| | | | |
|---|---|---|---|
| 2,990,253 A | 6/1961 | Smelby | |
| 3,880,590 A * | 4/1975 | Ogawa .................. | G01N 33/64 422/420 |
| 4,147,514 A | 4/1979 | Magers et al. | |
| 4,440,724 A * | 4/1984 | Tabb ....................... | G01N 33/64 422/420 |
| 4,844,867 A | 7/1989 | Bather | |
| 4,931,404 A | 6/1990 | Kundu | |
| 4,970,172 A | 11/1990 | Kundu | |
| 5,071,769 A | 12/1991 | Kundu et al. | |
| 5,174,959 A | 12/1992 | Kundu et al. | |
| 5,465,728 A | 11/1995 | Phillips | |
| 5,834,626 A | 11/1998 | De Castro et al. | |
| 6,010,459 A | 1/2000 | Silkoff et al. | |
| 6,067,989 A | 5/2000 | Katzman | |
| 6,190,858 B1 | 2/2001 | Persaud | |
| 6,206,837 B1 | 3/2001 | Brugnoli | |
| 6,221,026 B1 | 4/2001 | Phillips | |
| 6,234,006 B1 | 5/2001 | Sunshine et al. | |
| 6,254,547 B1 | 7/2001 | Phillips | |
| 6,454,723 B1 | 9/2002 | Montagnino | |
| 6,540,691 B1 | 4/2003 | Phillips | |
| 6,582,376 B2 | 6/2003 | Baghdassarian | |
| 6,599,253 B1 | 7/2003 | Baum et al. | |
| 6,607,387 B2 | 8/2003 | Mault | |
| 6,629,934 B2 | 10/2003 | Mault et al. | |
| 6,658,915 B2 | 12/2003 | Sunshine et al. | |
| 6,726,637 B2 | 4/2004 | Phillips | |
| 6,841,391 B2 | 1/2005 | Lewis et al. | |
| 6,981,947 B2 | 1/2006 | Melker | |
| 7,052,854 B2 | 5/2006 | Melker et al. | |
| 7,104,963 B2 | 9/2006 | Melker et al. | |
| 7,220,387 B2 | 5/2007 | Flaherty et al. | |
| 7,300,408 B2 | 11/2007 | Hancock et al. | |
| 7,364,551 B2 | 4/2008 | Allen et al. | |
| 7,533,558 B2 | 5/2009 | Flaherty et al. | |
| 7,727,369 B2 | 6/2010 | Kühn | |
| 7,794,994 B2 | 9/2010 | Cranley et al. | |
| 7,837,936 B1 | 11/2010 | Martin | |
| 7,920,998 B2 | 4/2011 | Brown | |
| 7,976,467 B2 | 7/2011 | Young et al. | |
| 8,021,308 B2 | 9/2011 | Carlson et al. | |
| 8,036,708 B2 | 10/2011 | Oozeki | |
| 8,286,088 B2 | 10/2012 | Shaffer et al. | |
| 8,287,454 B2 | 10/2012 | Wolpert et al. | |
| 8,342,178 B2 | 1/2013 | Hengstenberg et al. | |
| 8,399,837 B2 | 3/2013 | Robbins et al. | |
| 8,514,086 B2 | 8/2013 | Harper et al. | |
| 8,680,974 B2 | 3/2014 | Meiertoberens et al. | |
| 8,722,417 B2 | 5/2014 | Ahmad | |
| 8,816,862 B2 | 8/2014 | Harper et al. | |
| 8,848,189 B2 | 9/2014 | Atkin et al. | |
| 8,871,521 B2 | 10/2014 | Akers | |
| 8,917,184 B2 | 12/2014 | Smith et al. | |
| 9,170,225 B2 | 10/2015 | Dutta et al. | |
| 9,173,595 B2 | 11/2015 | Böhm et al. | |
| 9,518,991 B2 | 12/2016 | Ahmad et al. | |
| 2003/0208133 A1* | 11/2003 | Mault ................. | A61B 5/0002 600/532 |
| 2004/0018114 A1 | 1/2004 | Wang et al. | |
| 2007/0245810 A1 | 10/2007 | Carter et al. | |
| 2007/0258894 A1 | 11/2007 | Melker et al. | |
| 2008/0008666 A1 | 1/2008 | Phillips | |
| 2008/0053194 A1 | 3/2008 | Ahmad | |
| 2008/0234553 A1 | 9/2008 | Urman et al. | |
| 2009/0054799 A1 | 2/2009 | Vrtis et al. | |
| 2009/0290161 A1* | 11/2009 | Atkin ..................... | G01N 21/78 356/433 |
| 2010/0301197 A1 | 12/2010 | Boyle | |
| 2011/0028091 A1 | 2/2011 | Higgins et al. | |
| 2011/0098590 A1 | 4/2011 | Garbutt et al. | |
| 2012/0071737 A1 | 3/2012 | Landini et al. | |
| 2012/0295595 A1 | 11/2012 | Gibori et al. | |
| 2013/0231711 A1 | 9/2013 | Kaib | |
| 2013/0253358 A1 | 9/2013 | Phillips | |
| 2014/0276100 A1 | 9/2014 | Ahmad et al. | |
| 2014/0366610 A1 | 12/2014 | Rodriguez | |
| 2015/0073233 A1 | 3/2015 | Rich et al. | |
| 2015/0168307 A1 | 6/2015 | Kück et al. | |
| 2015/0289782 A1 | 10/2015 | Peverall et al. | |
| 2016/0146779 A1 | 5/2016 | Gallagher et al. | |
| 2016/0150995 A1 | 6/2016 | Ratto et al. | |

FOREIGN PATENT DOCUMENTS

| | | |
|---|---|---|
| WO | WO 03/039367 | 5/2003 |
| WO | WO 03/039483 | 5/2003 |
| WO | WO 2005/082234 | 9/2005 |
| WO | WO 2010/094967 | 8/2010 |
| WO | WO 2011/104567 | 9/2011 |
| WO | WO 2013/172873 | 11/2013 |
| WO | WO 2015/134390 | 9/2015 |

OTHER PUBLICATIONS

Barnett, D. et al., "Breath acetone and blood sugar measurements in diabetes", Clinical Science, vol. 37 (1969), in 1 page.

"CMS Operator Guide", CMS Operator Training 0108, dated Apr. 19, 2002, in 10 pages. URL: http://www.buydraegertubes.com/ds/cms-ops-guide.pdf.

Crofford, O., et al., "Acetone in Breath and Blood", Transactions of the American Clinical and Climatological Association, vol. 88 (1977), in 12 pages.

Diskin, A. et al., "Time variation of ammonia, acetone, isoprene and ethanol in breath: a quantitative SIFT-MS study over 30 days", Physiological Measurement, vol. 24 (2003), in 13 pages.

Dräger CMS Production Information (document properties of document indicate that the document was created on Dec. 1, 2008), in 4 pages. URL: http://www.draeger.com/sites/assets/PublishingImages/Products/cin_chip_measurement_system/US/cms-ds-pi-9044337-en-us.pdf.

DrägerTubes & Accuro Pump Production Information (document properties of document indicate that the document was created on Nov. 11, 2008), in 4 pages. URL: http://www.draeger.com/sites/assets/PublishingImages/Products/cin_accuro/US/081209-pi-DetectorTubes-22-10-2008-en.pdf.

(56) References Cited

OTHER PUBLICATIONS

Dubowski, K. et al., "Response of Breath-Alcohol Analyzers to Acetone: Further Studies", Journal of Analytical Toxicology, vol. 8, Sep./Oct. 1984, in 4 pages.
Gervais, T. et al., "Mass transport and surface reactions in microfluidic systems", Chemical Engineering Science, vol. 61 (2006), in 20 pages.
Ketonix US, "Ketonix 2015 Blue Specifications", 2015, in 2 pages. URL:https://www.ketonix.com/index.php/product-2/ketonix-2015-blue.
Ketonix, "Ketonix data for Michel Lundell", 2015, in 1 page. URL: https://www.ketonix.com.
Khan, A. et al. "Evaluation of a bedside blood ketone sensor: the effects of acidosis, hyperglycaemia and acetoacetate on sensor performance", Diabetic Medicine, vol. 21 (2004), in 5 pages.
Kundu, S. et al., "Breath Acetone Analyzer: Diagnostic Tool to Monitor Dietary Fat Loss", Clinical Chemistry, vol. 39 (1993), in 6 pages.
Kundu, S. K. et al., "Novel Solid-Phase Assay of Ketone Bodies in Urine", Clinical Chemistry, vol. 37 (1991), in 5 pages.
Kupari, M. et al., "Breath Acetone in Congestive Heart Failure", The American Journal of Cardiology, vol. 76, Nov. 15, 1995, in 3 pages.
Landini, B. et al., "Breath Acetone Concentration Measured Using a Palm-Size Enzymatic Sensor System", IEEE Sensors Journal, vol. 9, Dec. 2009, in 6 pages.
Landini, B. et al., "Effect of Exhalation Variables on the Current Response of an Enzymatic Breath Acetone Sensing Device", IEEE Sensors Journal, vol. 10, Jan. 2010, in 6 pages.
Likhodii, S., et al., "Breath Acetone as a Measure of Systemic Ketosis Assessed in a Rat Model of the Ketogenic Diet", Clinical Chemistry, vol. 48 (2002), in 6 pages.
Loken, S. C., "Breath Acetone and Ketone Metabolism in Obese and Diabetic Mice", Diabetes, vol. 25 (1976), in 1 page.
"Figaro Gas Sensor TGS 822", Figaro Engineering Inc., Mar. 1987, in 10 pages.
"MiniMed 530G System User Guide", Medtronic MiniMed, Inc., 2012, in 312 pages.
"Metron Package Insert", Akers Biosciences, Inc., 2013, in 2 pages.
Musa-Veloso, K. et al., "Breath acetone is a reliable indicator of ketosis in adults consuming ketogenic meals", The American Journal of Clinical Nutrition, vol. 76 (2002), in 6 pages.
Schwarz, K., et al., "Breath acetone—aspects of normal physiology related to age and gender as determined in a PTR-MS study", Journal of Breath Research, vol. 3 (2009), in 9 pages.
Swinehart, J. H., "The Nitroprusside Ion", Coordination Chemistry Reviews, Dec. 1967, in 18 pages.
Wang, L. et al., "Nanosensor Device for Breath Acetone Detection", Sensor Letters, vol. 8 (2010), in 4 pages.
Wang, L., "Tailored synthesis and characterization of selective metabolite-detecting nanoprobes for handheld breath analysis", Dissertation Ph. D. Thesis, Stony Brook University, Dec. 2008, in 127 pages.
Yoon, S. et al., "Active control of the depletion boundary layers in microfluidic electrochemical reactors", Lab on a Chip, vol. 6 (2006), in 9 pages.
International Search Report and Written Opinion for Application No. PCTUS2013000135 dated Jan. 16, 2014.
Pedersen, Ole. Pharmaceutical Chemical Analysis: Methods for Identification and Limit Tests, CRC Press, 2006, Chapter 3, obtained on Jun. 23, 2015.
Search Report in EP Patent Application No. 13790896.8 dated Jan. 29, 2016 in 9 pages.
U.S. Appl. No. 61/593,862, filed Feb. 1, 2012, Ahmad et al.

* cited by examiner

Step 1: Acetone reacts with APTES

Acetone
 N
 |

Step 2: Developer solution with SNP is added and SNP reacts with acetone/ primary amine to form color product Acetone
    NSNP
 |

METHOD AND APPARATUS FOR ANALYZING ACETONE IN BREATH

INCORPORATION BY REFERENCE TO ANY PRIORITY APPLICATIONS

This application is a continuation of U.S. patent application Ser. No. 14/400,911, filed Nov. 13, 2014, which is the national phase under 35 U.S.C. § 371 of PCT International Application No. PCT/US2013/000135, which has an International filing date of May 15, 2013, which claims the benefit of U.S. Provisional Application Nos. 61/792,158, filed on Mar. 15, 2013, and 61/646,924, filed on May 15, 2012. The disclosures of the aforementioned applications are hereby incorporated in their entirety herein by reference. Any and all priority claims identified in the Application Data Sheet, or any correction thereto, are hereby incorporated by reference under 37 CFR 1.57.

FIELD OF THE INVENTION

The present invention relates generally to methods, apparatus and technology for analyzing acetone in the breath of a living thing, preferably a human.

BACKGROUND OF THE INVENTION

Ketone bodies include acetoacetic acid (beta-ketobutyric acid, diacetic acid), beta-hydroxybutyric acid, and acetone. For purposes of gas analysis, acetone is the most important of these, given its relatively high vapor pressure. The advantages of analyzing acetone, or other ketone bodies or ketones, in breath are well recognized and have been for decades. Under normal, unstressed physiological circumstances, for example, the body metabolizes primarily carbohydrates. When normal carbohydrate metabolism is impaired, however, the body begins to metabolize fats or fatty acids. During fat metabolism, ketone bodies including acetone are produced as intermediaries and begin to accumulate in body fluids such as blood and urine. As the accumulated ketone bodies are transported in the blood, they become involved the gas exchange in the alveolar spaces of the lungs. This is particularly true of acetone, given its low molecular weight and vapor pressure. As a result of this pulmonary transport, the acetone appears in the breath, including expired breath, where it can be analyzed. The term "analyze" as used herein is used in is common but broad sense to include such things as detection of the presence of a chemical component. It also may include measurement of concentration or of properties or conditions of the component.

The ability to analyze acetone and in some cases other ketone bodies or ketones is important in health care. An accumulation of acetone or ketone bodies is generally referred to as "ketosis" or "ketoacidosis." These conditions can have toxic effects and in extreme cases can lead to permanent injury or death. Patients suffering from diabetes mellitus, for example, are susceptible to ketoacidosis.

During ketoacidosis, elevated levels of ketone bodies occur in body fluids, mainly in blood, urine and breath. The primary means for testing to identify these elevated ketone body levels has been through blood and/or urine analysis.

A common and well known technique for analyzing ketone bodies in blood and urine is the so-called "Legal test," in which appropriately soluble nitroprussides are used to react with and correspondingly detect certain ketone bodies. Swinehart, *Coordination Chem. Rev.*, 2(4), 386-403 (December 1967) is often cited. It discloses a summary of work undertaken on the reaction of sodium nitroprusside with acetone and aceoacetic acid. He described a mechanism of reaction in which the sodium nitroprusside reacts at the site of the acidic hydrogen, and action of the nitrosyl moiety of sodium nitroprusside.

U.S. Pat. No. 2,186,902, issued to Fortune on Jan. 9, 1940, discloses the use of nitroprusside wherein the reaction is carried out in the presence of ammonia to develop and utilize color-based detection features. U.S. Pat. No. 2,509,140 discloses a nitroprusside reaction in urine wherein the reaction takes place in the presence of an aliphatic amino acid, i.e., glycine, and an alialkine material. U.S. Pat. No. 2,900,253, issued to Smeby on Jun. 27, 2961, discloses a test method that use of dip sticks or swabs chemically treated with a nitroprusside to obtain a sample of the blood or urine and test for the presence of ketone bodies.

In contrast to ketone body testing in blood and urine, the use of breath for ketone body analysis has been far more limited. Abbott Laboratories, in several issued patents, disclosed methods for detecting acetone in breath using nitroprusside and a primary amine. See, e.g., U.S. Pat. Nos. 4,970,172, 5,071,769 and 5,174,959. As reported therein, Abbott used a tertiary amine with a pH of 4.5 and a primary amine without any adjustment pH. Methods disclosed therein used a developer solution with 0.5% diethanolamine in 25% dimethylsulfoxide and 75% methanol. While the overall concept reportedly was able to detect acetone in breath, it had a long manufacturing time (four days), a long reaction time (18 minutes), a large consumable materials requirement with relatively expensive reagents packed inside, and was not adequately stable over long periods of time. Although the device disclosed by Abbott reportedly was operable, it was not commercially feasible.

A pronounced problem encountered in nitroprusside-based tests for ketone bodies in general lies in the instability of the nitroprusside. As is noted in U.S. Pat. No. 2,990,253, for example, sodium nitroprusside is very unstable in an aqueous, alkaline medium. Unfortunately, however, this is precisely the type of medium that is required to achieve the desired reaction between the ketone (in that case sodium acetoacetate) and sodium nitroprusside.

The solution to this instability problem proposed and claimed in U.S. Pat. No. 2,990,253 involved preparation of a stick test using a two-step approach. The first step involved applying the nitroprusside to a carrier in an acidic aqueous medium, and drying. The second involved dipping the carrier into a non-aqueous solution of organic bases, such as various amines, aminoalcohols or mixtures thereof, to achieve the alkalinity needed for the desired reaction with the ketone body. The aqueous solution comprised sodium nitroprusside, glycine, monosodium phosphate-monohydrate, disodium phosphate and sodium chloride. The second step comprised using a secondary or tertiary amine or aminoalcohol or a mixture thereof in anhydrous ethanol or chloroform.

U.S. Pat. No. 4,147,514, issued to Magers et al. on Apr. 3, 1979, suggests addressing the instability problem by using nitroprusside in combination with at least one primary amine, and a metal salt. The metal salt reportedly stabilized the nitroprusside in solution at alkaline pH ranges, allowed for a single-dip production method, promoted ionization of the ketone bodies, resulted in a shorted reaction time, and stabilized the resulting chromophoric complex.

Abbott, e.g., in the aforementioned patents, noted that the color complex is unstable because nitroprusside decomposes rapidly in alkaline solutions, and that nitroprusside salts are subject to decomposition in the presence of moisture and high pH. According to Abbott, these limitations have led to numerous attempts to stabilize the color complex by utilizing mixtures of nitroprussides and amines or amino acids in combination with a variety of buffers, metal salts, organic salts, organic stabilizers and polymers. Abbott then provided a summary of efforts by various parties as reported in various issued patents aimed to addressing this problem. Abbott proposed the use of a first solid matrix material to which a nitroprusside salt is coupled, and a second solid matrix material to which an amine is covalently bound. Abbot also proposed the addition of magnesium or calcium salts to promote chelate formation and to stabilize the color products and enhance the kinetics of the reaction between the carbonyl compound, the amine and the nitroprusside.

Notwithstanding these efforts, the stability of the nitroprusside-based test regimes as described herein above have persisted and have limited the use of such regimes for the analysis of ketone bodies in breath and other gases. Abbott, for example, apparently never advanced its breath acetone product development to commercial fruition.

SUMMARY OF THE INVENTION

The present inventions according to its various aspects provide methods and apparatus for detecting or otherwise analyzing ketone bodies, particularly acetone, in breath using primary amines and nitroprusside, which methods and apparatus provide enhanced stability, enhanced response time, and/or enhanced chromic qualities.

In accordance with one aspect of the invention, a method for is provided for analyzing acetone in breath. The method comprises providing a cavity, locating within the cavity a primary amine disposed on a first surface, and locating within the cavity a nitroprusside on a second surface distinct from the first surface. The nitroprusside is coupled to the second surface using a coupling agent comprising an anion exchange resin in an acidic environment, wherein the acid environment comprises an acid having a vapor pressure of less than about 1 atmosphere at 22 C when in its 99% pure form. The primary amine on the first surface and the nitroprusside on the second surface comprising cavity contents having a reference optical property. The method further comprises causing the breath to move into the cavity so that it contacts the primary amine and the nitroprusside to cause or facilitate a change in an optical property of the cavity contents relative to the reference optical property. It also comprises analyzing the breath for the presence of the acetone using the change in the optical property.

The cavity preferably but optionally comprises an elongated and enclosed channel. It preferably contains the primary amine on the first surface and the nitroprusside on the second surface in the form of a packed bed.

The breath typically comprises a moisture content, and the method may further comprise pretreating the breath prior to causing the breath to contact the primary amine to reduce the moisture content.

The primary amine preferably has a pKb of less than 5. A presently preferred primary amine comprises an amino silane.

The first surface preferably comprises a plurality of beads comprised of silica, quartz, aluminum oxide, alumino-silicates, silicon, copper, tin oxide, talc, inorganic oxides, or combinations thereof.

The nitroprusside preferably comprises sodium nitroprusside. The second surface preferably comprises a plurality of beads comprised of silica, quartz, aluminum oxide, alumino-silicates, silicon, copper, tin oxide, talc, inorganic oxides, or combinations thereof. The coupling agent may comprise a tertiary amine, and preferably comprises diethylaminopropyl trimethoxysilane. The acidic environment preferably comprises sulfuric acid, and substantially excludes hydrochloric acid.

The reference optical property preferably comprises a reference color and the change in optical property preferably comprises a change in color with respect to the reference color. The cavity in presently preferred embodiments and methods has a linear dimension, the reference optical property preferably comprises a reference distance of the reference color along the linear dimension, and the change in optical property preferably comprises a measured distance along the linear dimension of the change in color with respect to the reference color. The method may comprise introducing a developer solution into the cavity to facilitate the change in the optical property.

In accordance with another aspect of the invention, a method is provided for analyzing acetone in breath. This method comprises providing a cavity, locating within the cavity a primary amine disposed on a first surface, and locating within the cavity a nitroprusside on a second neutral surface distinct from the first surface. The nitroprusside is in a dry state. The primary amine on the first surface and the nitroprusside on the second surface comprise cavity contents having a reference optical property. The method also comprises causing the breath to move into the cavity so that it contacts the primary amine and the nitroprusside to cause or facilitate a change in an optical property of the cavity contents relative to the reference optical property, and analyzing the breath for the presence of the acetone using the change in the optical property.

Preferred features of the first aforementioned also apply to this method.

The nitroprusside on the second neutral surface may be attached to the second surface without use of a coupling agent. It may be adsorbed or dried onto the second neutral surface, or otherwise be disposed thereon without a chemical bond.

The nitroprusside on the second surface preferably is initially located fluidically separately from the primary amine on the first surface, and the method comprises sequentially reacting the breath with the primary amine to yield a reaction product, and then contacting the nitroprusside with the reaction product. The method also may comprise introducing a developer solution into the cavity to facilitate the change in the optical property.

In accordance with another aspect of the invention, a method is provided for analyzing acetone in breath, wherein the method comprises providing a cavity, and locating within the cavity a primary amine disposed on a first surface. The primary amine on the first surface comprises cavity contents having a reference optical property. The method also comprises providing a nitroprusside in a nitroprusside solution initially separated from the primary amine on the first surface, wherein conditions of the nitroprusside solution when separated from the primary amine on the first surface are selected to stabilize the nitroprusside relative to the reactivity of the nitroprusside in the cavity with the primary amine. The method further comprises causing the breath to move into the cavity so that it contacts the primary amine to create a primary amine reaction product, and causing the nitroprusside solution to enter the cavity and the nitroprusside to react with at least one of the acetone and the primary amine reaction product, to cause or facilitate a change in an optical property of the cavity contents relative to the reference optical property, and analyzing the breath for the presence of the acetone using the change in the optical property.

The optional but preferred aspects of the invention noted herein above also may apply to this aspect of the invention. It is also preferable that the providing of a nitroprusside in a nitroprusside solution initially separated from the primary amine on the first surface comprises preventing light from contacting the nitroprusside solution, and also may comprise limiting light from contacting the nitroprusside solution sufficiently that the effectiveness of the nitroprusside in reacting with at least one of the acetone and the primary amine reaction product and the causing or facilitating of the change in an optical property of the cavity contents relative to the reference optical property are not impaired.

In accordance with yet another aspect of the invention, a method is provided for analyzing acetone in breath. The method comprises preparing a surface upon which is disposed a primary amine and a nitroprusside. The preparation comprises disposing the primary amine and the nitroprusside in an acidic environment. The method also comprises locating the surface upon which is disposed the primary amine and the nitroprusside within a cavity. The surface comprising the primary amine and the nitroprusside comprises a reference optical property. The surface preferably is in proximate contact with a solution. The method further comprises causing the breath to move into the cavity so that it contacts the primary amine and the nitroprusside to cause or facilitate a change in an optical property of the surface relative to the reference optical property. The method further comprises analyzing the breath for the presence of the acetone using the change in the optical property.

Again, the optional but preferred features noted herein above also may apply to this aspect of the invention.

The acidic environment according to this aspect of the invention preferably has a pH of between 0 and 6, and more preferably has a pH of between 0.5 and 2.

The method also may comprise exposing the surface to a second solution, wherein the second solution comprises a base having a alkalinity at least as strong as an alkalinity of the primary amine, and wherein the base is present in a concentration sufficient to increase extent of the reaction and the change in the optical property of the surface beyond the extent of the reaction and change in the optical property in the absence of the second solution.

In various embodiments and method implementations of the invention according to one or more of these aspects, use preferably is made of relatively higher concentrations of nitroprusside on the surface to which it is immobilized or in solution. The higher concentrations drive the kinetics to improve reaction time and test response time, and can improve sensitivity. In addition, enhanced stability can be achieved in certain of these embodiments and implementations using such features as: (i) less volatile acids (e.g., $H_2SO_4$ instead of HCl), (ii) more acid (i.e., a lower pH), (iii) surfaces that are not inherently basic (e.g., avoiding the use of tertiary amines for supporting the nitroprusside), and (iv) protecting the nitroprusside from light or other degrading radiations.

In addition, and in accordance with another aspect of the invention, a cartridge is provided for containing the reagents, e.g., such as those described herein, and for practicing methods as described herein and the like.

In presently preferred embodiments and method implementations according to these various aspects of the invention, one can achieve faster manufacturing times (e.g., less than four hours), faster reaction times (e.g., less than six minutes), lower cost and/or greater stability relatively to prior known and reported methods and devices. These features or results also can be achieved in the form of relatively small, portable devices that are relatively inexpensive, easy to use and are amenable to field or patient home use.

In accordance with another aspect of the invention, a method is provided for sensing acetone in breath using a breath analysis device. The method comprises disposing a reactant in a reaction zone within the breath analysis device, wherein the reactant comprises a primary amine disposed on a surface, and wherein the reaction zone has an optical characteristic that is at a reference level. It also comprises pre-storing a liquid nitroprusside solution within the breath analysis device separately from the reactant. The method further comprises using the breath analysis device to cause the breath to contact the reactant in the reaction zone so that the acetone in the breath reacts with the reactant to form a reaction product and, after the reaction product has been formed, using the breath analysis device to cause the nitroprusside solution to contact and react with the reaction product and to facilitate a change in the optical characteristic of the reaction zone relative to the reference level. The method also comprises using the breath analysis device to detect the change in the optical characteristic to sense the acetone in the breath.

Optionally, causing the nitroprusside solution to contact the reaction product has an optical characteristic that is at a second reference level. Then, causing the nitroprusside solution to react with the reaction product facilitates a change in the optical characteristic of the reaction zone relative to the second reference level.

Optionally but preferably, the surface comprises a silica gel, and more preferably a plurality of silica gel beads, preferably having a size distribution between 100 and 270 mesh.

It is also preferred that the disposing of the reactant in the reaction zone comprises maintaining the reactant in an alkaline environment. The disposing of the reactant in the reaction zone also may comprise maintaining the reactant in the absence of volatile acid, or quenching the primary amine with a non-volatile acid. An example of a non-volatile acid would be sulfuric acid.

The pre-storing of the liquid nitroprusside solution within the breath analysis device separately from the reactant preferably comprises providing the liquid nitroprusside solution to consist essentially of a non-alkaline solution. It also may and preferably does comprise providing the liquid nitroprusside solution in the absence of a substance with a base dissociation constant less than 6.

The pre-storing of the liquid nitroprusside solution also may comprise quenching the liquid nitroprusside solution with a non-volatile acid, such as sulfuric acid. This quenching preferably is undertaken so that the liquid nitroprusside solution has a pH of less than 8, and more preferably below 7.

It is also preferably that the liquid nitroprusside solution be stored in the absence of ambient light.

In accordance with still another aspect of the invention, a method is provided for sensing acetone in breath using a breath analysis device. The method comprises disposing a reactant in a reaction zone within the breath analysis device, wherein the reactant comprises a primary amine disposed on a surface, and wherein the reaction zone has an optical characteristic that is at a reference level, pre-storing a nitroprusside in the breath analysis device in a non-alkaline environment, and using the breath analysis device to cause the breath to contact the reactant in the reaction zone so that the acetone in the breath reacts with the primary amine to form a reaction product. After the reaction product has been formed, the method further comprises using the breath analysis device to cause the nitroprusside to contact and react with the reaction product and to facilitate a change in the optical characteristic of the reaction zone relative to the reference level, and using the breath analysis device to detect the change in the optical characteristic and to sense the acetone in the breath.

The disposing of the reactant in the reaction zone within the breath analysis device optionally but preferably comprises quenching the primary amine on the surface with a non-volatile acid so that the primary amine on the surface has a pH that is less than 8, and more preferably less than 7. An example of a suitable non-volatile acid is sulfuric acid.

The pre-storing of the nitroprusside in the breath analysis device in a non-alkaline environment preferably comprises pre-storing the nitroprusside separately from the reactant prior to the causing of the nitroprusside to contact the primary amine reaction product, preferably using a gas-tight barrier.

The pre-storing of the nitroprusside in the breath analysis device in a non-alkaline environment preferably comprises pre-storing the nitroprusside in the absence of a substance with a base dissociation constant less than 6.

The pre-storing of the nitroprusside in the breath analysis device in a non-alkaline environment preferably comprises quenching the nitroprusside with a non-volatile acid, such as sulfuric acid. The pre-storing of the nitroprusside in the breath analysis device in a non-alkaline environment also preferably comprises quenching the nitroprusside with a non-volatile acid so that the environment has a pH is below 8, and more preferably below 7.

In one embodiment, the primary amine is disposed on a first surface, e.g., silica gel beads, the nitroprusside is disposed on a second surface other than the first surface, such as silica gel beads having the nitroprusside but not the primary amine, and the first and second surfaces, e.g., the two sets of beads, are intermingled prior to the causing of the nitroprusside to contact the reaction product. In this setting, the causing of the nitroprusside to contact and react with the reaction product preferably comprises dispensing a liquid developer solution to contact the first and second surfaces, or intermingled beads.

In another alternate embodiment the nitroprusside is coupled to the reactant prior to the causing of the nitroprusside to contact the primary amine product. The reactant and the nitroprusside are disposed in the non-alkaline environment, and the causing of the nitroprusside to contact and react with the reaction product comprises dispensing a liquid developer solution to contact the nitroprusside and the reaction product.

BRIEF DESCRIPTION OF DRAWINGS

The accompanying drawings, which are incorporated in and constitute a part of the specification, illustrate a presently preferred embodiments and methods of the invention and, together with the general description given above and the detailed description of the preferred embodiments and methods given below, serve to explain the principles of the invention. Of the drawings.

DETAILED DESCRIPTION OF PREFERRED EMBODIMENTS AND METHODS OF THE INVENTION

Figure 1:
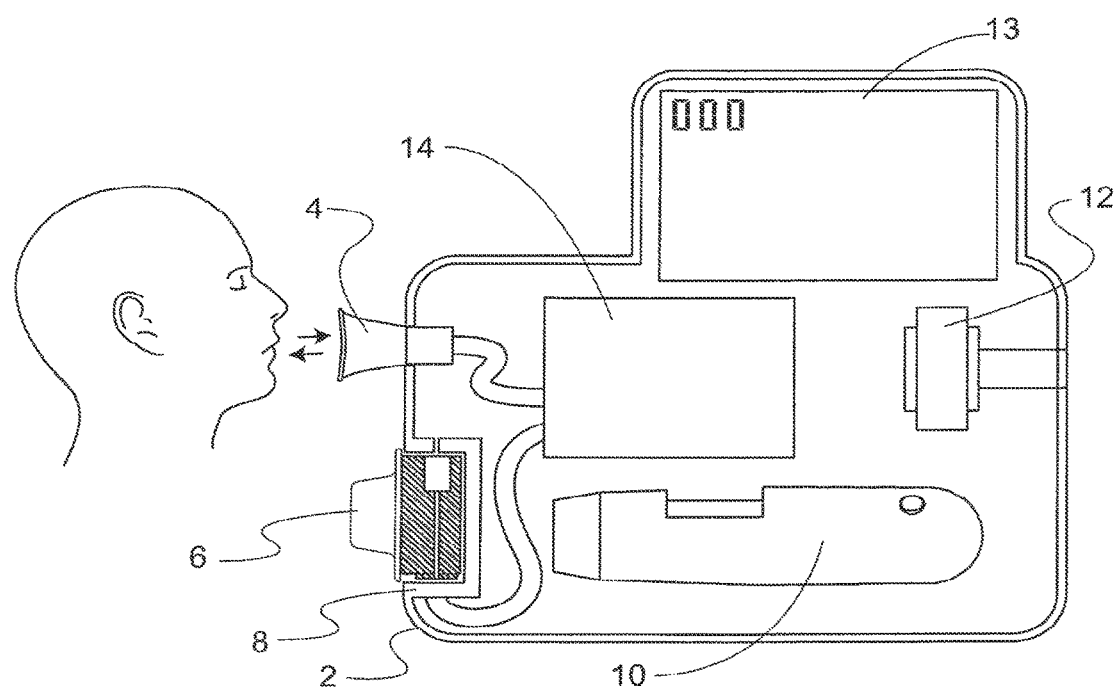
FIG. 1 shows a composite illustration of a device and disposable cartridge used in detecting colorimetric changes from reactions with breath analytes.
Figure 1:
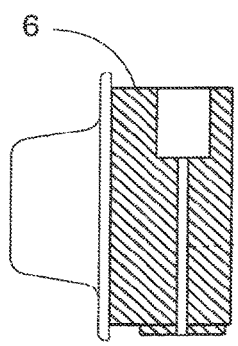

Reference will now be made in detail to the presently preferred embodiments and methods or method implementations of the invention as described herein below and as illustrated in the accompanying drawings, in which like reference characters designate like or corresponding parts throughout the drawings. It should be noted, however, that the invention in its broader aspects is not limited to the specific details, representative devices and methods, and illustrative examples shown and described in this section in connection with the preferred embodiments and methods. The invention according to its various aspects is particularly pointed out and distinctly claimed in the attached claims read in view of this specification, and appropriate equivalents.

To better appreciate and illustrate the various aspects of the invention as set forth herein, some background on the general reaction of ketone bodies using a nitroprusside color reaction test regime is useful and instructive. Reactions of nitroprusside to analyze ketone bodies, e.g., the Legal test, generally take place under the following reaction regime. There are two primary reactants are used: (1) one or more primary amines, and (2) the nitroprusside. In preferred regimes known and reported publicly, such as those disclosed by Abbott, each of these reactants is immobilized on a separate surface, typically using solid-phase beads, although it is possible to put both reactants on the same surface. The surfaces are usually in the same reaction zone.

The reaction dynamics involve the following steps:

1. Acetone is introduced into the reaction zone. The acetone or other ketone body contacts the primary amine or amines on the first surface, whereupon the acetone reacts with the primary amine(s) to form a Schiff base.

2. A solvent or "developer solution" is introduced into the reaction zone. The solvent solubilizes the Schiff base and the nitroprusside.

3. The Schiff base reacts with the nitroprusside to yield a color product. This reaction causes a color change, from reactant to product. The specific color indicates the presence of the reactant, i.e., acetone. The extent of advance through the reaction zone indicates the concentration of the acetone in the breath sample.

While a number of nitroprusside based ketone detection urinalysis and blood based methods have been described in the prior art, none of these is believed to be capable of detecting acetone, especially not as it is present in breath. While reactions with acetone have been reported, what they are appears to be occurring is a reaction with ketone bodies acetoacetic acid and/or beta-hydroxybutyrate (b-HBA). The water present in urine and blood inhibits visible color change from acetone at levels present in the body. Even the humidity in normal breath is sufficient to prevent color formation in a reaction between acetone, a primary amine and nitroprusside.

Given the much slower and weaker reaction of acetone with primary amines and nitroprusside, a variety of changes to the chemistry and reaction methods must be made to enable detection at levels present in breath. First, all or essentially all traces of water must be removed from the breath sample. This can be accomplished through a variety of drying methods, including but not limited to the use of desiccants. Preferred desiccants include ascarite, sodium hydroxide, and calcium chloride. Large calcium chloride particles do not provide sufficient surface area to extract humidity in a small chamber. Smaller $CaCl_2$ particles are preferred, between about 20 and about 200 mesh, between about 30 and 100 mesh, between about 35 and 60 mesh.

Next, one must have a method for concentrating the acetone from breath up to detectable levels. This can be accomplished by passing the breath sample across a packed bed or similar high surface area medium with affinity for acetone. In preferred embodiments and methods according to the present invention, the component in the packed bed with affinity for acetone is the primary amine used to form the Schiff base with acetone. In order to force the breath through the packed bed, it is contained in such a fashion that a gas tight seal can be made and the sample has only one direction to flow. This can be accomplished by enclosing the affinity reagents for acetone in a cavity.

Flow rates scan be optimized in order to: 1) remove sufficient water content and 2) concentrate the acetone on a sufficiently small region of the packed bed to create the concentration necessary for a visible color change. Optimal flow rates depend on the amount and size of the desiccant and the dimensions of the packed bed. The flow rate preferably is sufficient to flush out dead volume and provide a good average acetone level in breath in less than 10 min, or more preferably in less than 5 min. Further, the flow rate must be slow enough that it does not use excessive desiccant or reagent, and does not require sample collection bags larger than 10 L, or more preferably larger than 1 L. Preferred flow rates are between about 10 and about 1000 mL/min, between about 50 and about 250 mL/min, between about 100 and 150 mL/min. Flow rates also preferably are constant, within plus or minus 30%, or more preferably 10%, or even more preferably, 1% of the target flow rate. This will provide consistent, repeatable color formation.

The reaction also should be more alkaline than is commonly used in urinalysis and blood tests for acetone. The alkalinity of the reaction should match the pKa of the conjugate acid of the primary amine in order to have rapid and sensitive reaction kinetics. Because nitroprusside degrades in alkaline environments, in presently preferred embodiments and methods it is either stored in a separate location from the primary amine or the pH is adjusted in a separate step. In either case, a separate developer solution is used to solvate the nitroprusside and/or to modify the pH of the reaction.

Each of the foregoing changes significantly improves the ability to detect acetone, especially at the concentrations at which acetone is present in breath. In contrast, none of these features is required for detection of acetoacetic acid and b-HBA in blood and urine. But because known urinalysis and blood testing methods do not incorporate the foregoing changes together, they are incapable of detecting acetone, especially at the concentrations present in breath.

Methods and devices according to the present invention preferably are implemented using a breath analysis device that is configured to carry out the methods as generally described herein and their equivalents. Although not necessarily limiting, U.S. Application No. 61/593,862 the ('862 application"), filed on Feb. 1, 2012 and commonly assigned to the present inventors' assignee, Invoy Technologies, LLC, provide various descriptions, illustrations and examples of devices and supporting methods upon which preferred embodiments and method implementations of the present invention may be carried out. The '862 application is hereby incorporated by reference as if fully set forth herein, and the reader is directed to that application for a description of details and alternate variations. It should be understood, however, that the present invention according to these aspects is not necessarily limited to such specific and illustrative devices and methods of that application.

Devices and methods according to the '862 application can include or incorporate any or all of a base, a breath input, an insertion mechanism for a cartridge, a sensing subsystem, a pneumatic handler, a reaction initiator, a kinetic enhancer, a breath conditioner, a digitizer, or a cartridge. Each of these components can also contain subcomponents. Any or all of the components can be contained within or otherwise coupled to the base. The base optionally forms a housing or a connection point for the other components that make up the breath analyzer device.

FIG. 1 shows a preferred but illustrative embodiment of a system for measuring at least one analyte in breath. The system comprises a base in the form of a base unit (2), dispensing device here in the form of an insertion mechanism (8) for a cartridge (6), an optical sensing subsystem (10), a flow facilitator, here specifically in the form of a pneumatic handler (12) and a digitizer (14). The base unit (2) receives breath from a user via a breath input (4). The insertion mechanism for a cartridge includes means for a cartridge to be inserted, where the cartridge contains a reactive chemistry capable of reacting with at least one analyte when present in the breath in concentrations of less than about 5 ppm to generate an optical change. The optical sensing subsystem measures an optical change. The pneumatic handler is preferably included within the base unit, although this is not always the case. The pneumatic handler allows for the breath to interact with the reactive chemistry in the cartridge. The digitizer quantifies the optical change measured by the optical sensing subsystem and outputs a display (13) containing information regarding the at least one analyte in the breath.

The base unit can be any apparatus that receives breath from a user. In certain embodiments, the base unit contains the pneumatic handler. In preferred embodiments, the base unit is portable and capable of individual patient use. The base unit may also be capable of withstanding (measuring and compensating for) temperature and humidity changes so as to improve the accuracy of the measurement process.

A breath input can be anything capable of receiving breath from a user, and optionally perform the function of breath metering. The breath input may optionally include the step of breath conditioning, but this may also be handled by the base unit itself. The breath input can also include breath sampling, which preferably utilizes a reservoir for containing the breath sample.

In general, breath collection involves the collection of breath in the form of a breath sample. Such breath collection may be direct or indirect. For improved relevance of the measurement results made by the breath analyzer, breath collection can be performed with attention to details such as: (a) total volume of breath collected; (b) source of collected breath (e.g., upper airways vs. alveolar air); (c) number of breaths collected; (d) physiological status of the subject prior to and during breath collection (e.g., rested state with normal breathing vs. active state with increased breath rate vs. hyperventilation, as examples); and (e) breathing effort of the sample collection mechanism (e.g., does the subject need to breath through a high-resistance collection apparatus at extended duration, or does the mechanism allow for normal breath exhalations).

Figure 2:
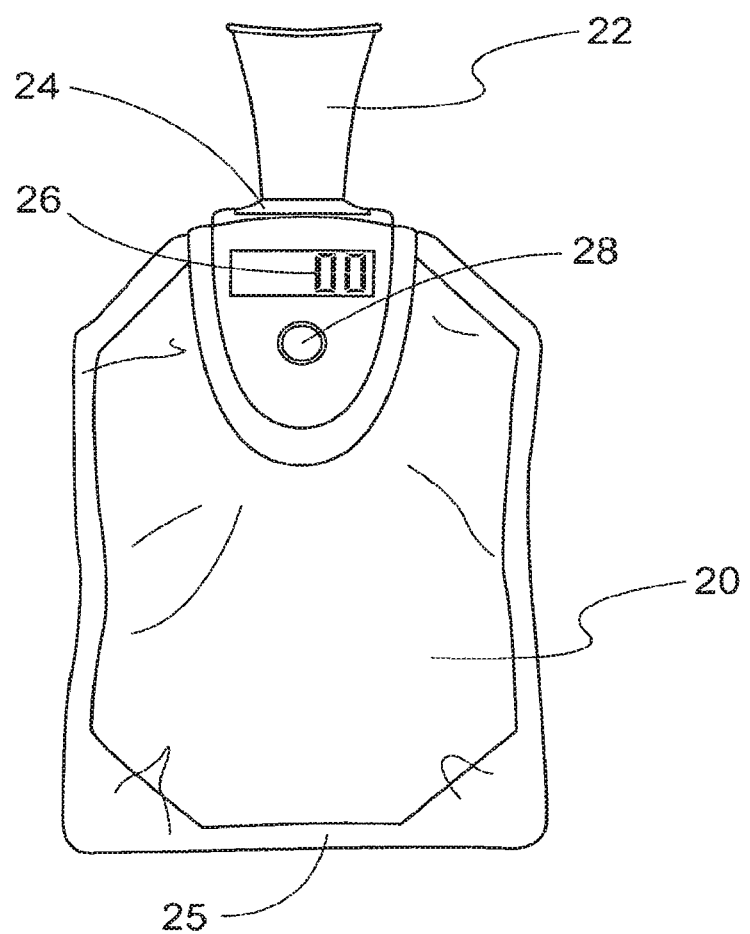
FIG. 2 shows an example of a breath collection bag with integrated flow measurement capabilities.
Figure 3:
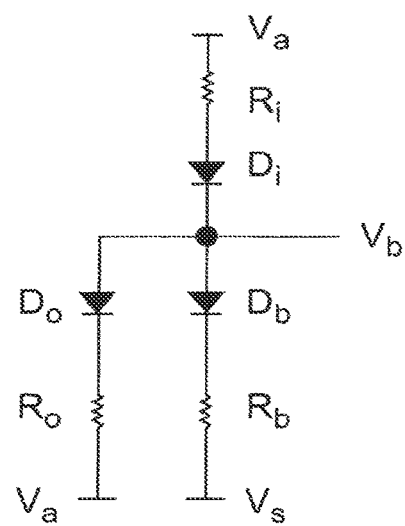
FIG. 3 demonstrates an example of an indirect breath collection performed by a breath input.
Figure 3:
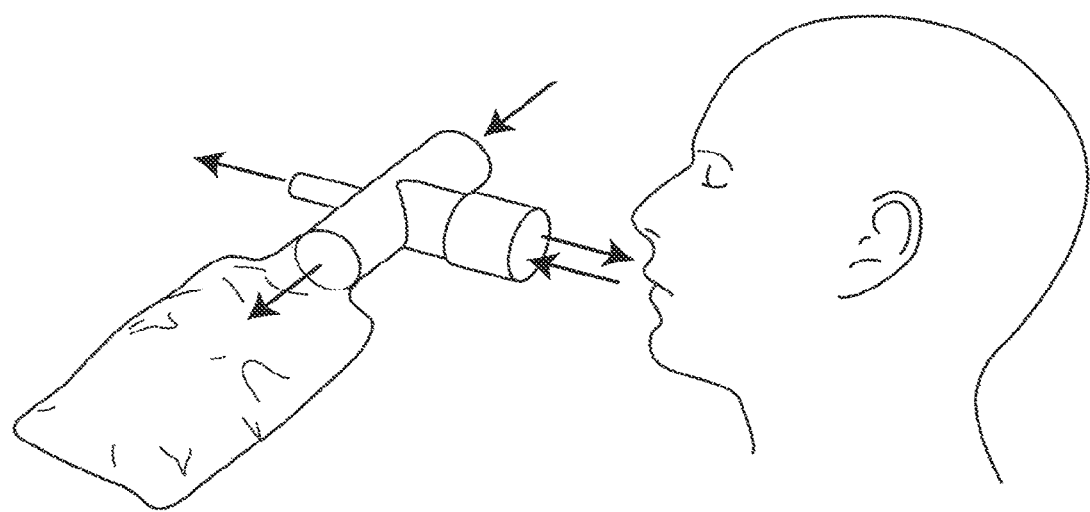

FIG. 2 shows an example of a breath collection bag with integrated flow measurement capabilities. A breath sampling bag (20) comprised of wall materials impermeable to the analytes of interest and in some cases also their ambient interferents contains a breathing inlet (24) fitted with a mouthpiece (22). An upper portion of the assembly houses electronics and/or mechanical devices useful in analyzing or conditioning breath samples, including in some cases a visual indicator (26). The electronics can consist of a variety of assets, including temperature probes, pressure transducers, timing circuits, humidity sensors, and others depending on the application. Mechanical devices can include one-way breathing valves, flow restrictors, scrubber or desiccant chambers, computer-controlled or automatic valves, manual valves, and others. In one embodiment, the one-way valve (24) is designed to mate with a receiver port on a base unit which is equipped with fingers or protrusions designed to open the one-way valve. This system enables a breath sample to be collected from a user and to be contained within the sampling bag without user interaction. Attaching the bag to the base unit allows the fingers or protrusions to open the one-way valve (for example, a flapper valve) so that the contents of the bag can be removed by, for example, a pneumatic handler of the base unit. No manual interaction with the valve is required by the user. Also shown in FIG. 2 is a user interface button (28), exemplifying a possible interaction of the user with the electronics, such as to start a timer. A second end of the bag (25) can be fitted with similar facilities. For example, fitting the lower portion (25) with a second one-way valve, such that the user breathes into a first one-way valve (24) and out through the second (25) results in the last exhaled portion of air being captured in the bag. This can be used to sample, for example, the deep alveolar airspace whereas without the second one-way valve the air collected is the first portion blown into the device. The bag may likewise be fitted at other points, for example on the sides or front/back faces.

It is often desirable to condition the breath prior to or as part of the analysis. Particular examples of breath conditioning include: (a) desiccation (e.g., removal of water); (b) scrubbing (e.g., removal of carbon dioxide or volatile organic compounds); and (c) heating or cooling of the gas stream (condensation prevention/instigation). The breath condition function, if performed, can be carried out by the breath input or a separate system.

The optical sensing subsystem can be any detector or other sensor that is capable of measuring an optical change. This may be a direct measurement of optical change. It may also be an indirect measurement of optical change (e.g., transduction through other energy states). The optical change may involve any of the following, alone or in combination, without limitation: reflectance, absorbance, fluorescence, chemiluminescence, bioluminescence, polarization changes, phase changes, divergences, scattering properties, evanescent wave and surface plasmon resonance approaches, or any other optical change known to those skilled in the art.

The optical sensing subsystem may be contained within the base unit or it may be a separate module that is plugged into the base unit. The optical sensing subsystem may be single use or it may be used multiple times. The optical sensing subsystem may also comprise an array of detectors that work in tandem to measure the optical change.

In system designs utilizing any of reflectance, absorbance and fluorescence, excitation light is supplied to the system and changes in that light are tracked in relation to changes in the chemical state of the sensor system. It is preferred to minimize the amount of unmodulated light that enters the sensing subsystem and to measure only the light that is being changed by the chemical system. For example, a chemical system that produces a maximum absorbance change at 400 nm is preferably implemented with excitation light at 400 nm as opposed to unfiltered broadband light sources such as incandescent lamps. However, if a base unit is intended to measure numerous chemistries with various spectral characteristics, broadband excitation sources may be preferable.

Excitation sources include, but are not limited to, incandescent lamps, such as tungsten filaments and halogen lamps; arc-lamps, such as xenon, sodium, mercury; light-emitting diodes, and lasers. Excitation light may benefit from conditioning efforts, such as filtering, polarization, or any of the other methods known by those skilled in the art. For example, allowing only light of the wavelength that matches the wavelength of the chemical system's peak response is useful in increasing the signal to noise ratio of the optical system.

Each of these modalities can be employed with spot interrogations as well as with scanning mechanisms, either one or two-dimensional. A scanning system can be useful in breath measurement devices, especially where analyte concentration varies along an axis and where that variation is indicative of analyte concentration in the breath.

Figure 4:
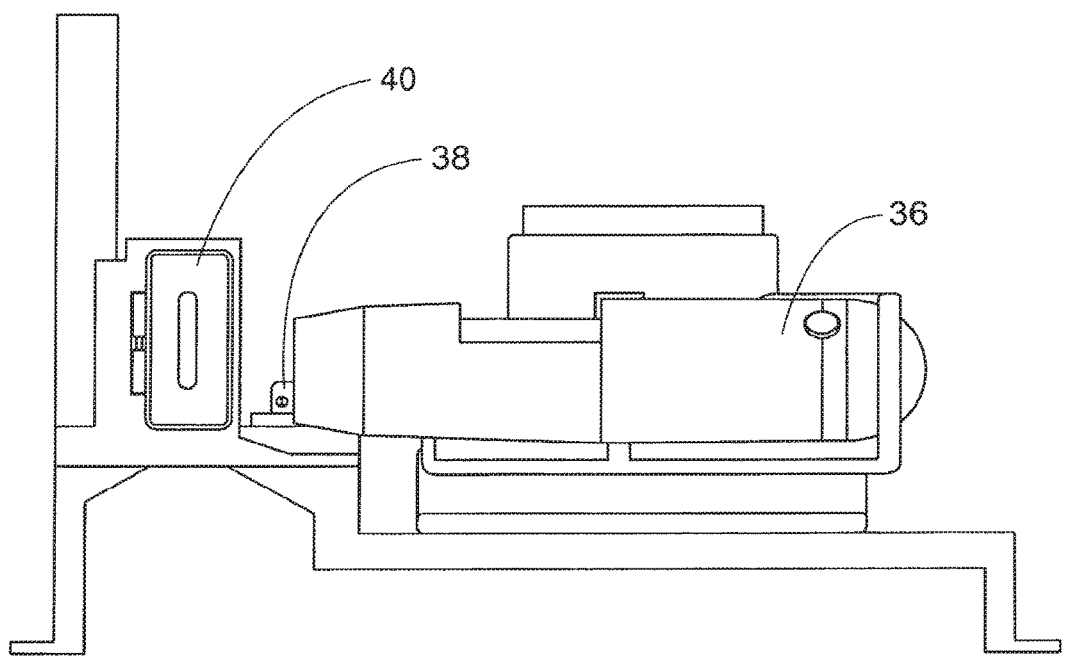
FIG. 4 depicts a general layout for an optical sensing subsystem configuration.
Figure 5:
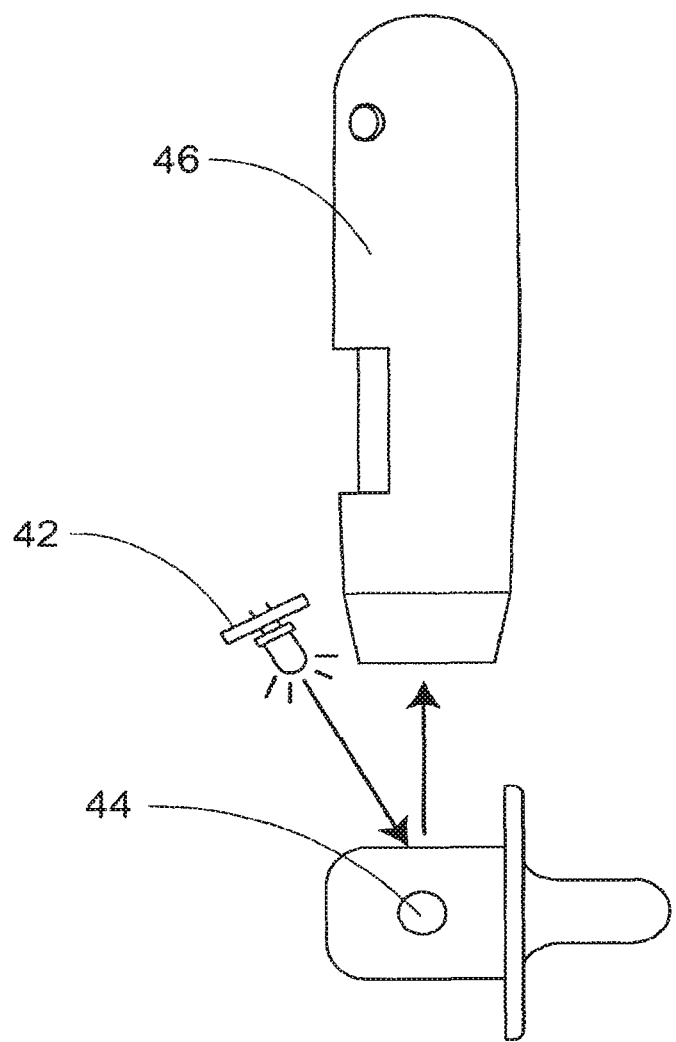
FIG. 5 depicts a general layout for an optical sensing subsystem configuration from a top-view.
Figure 6:
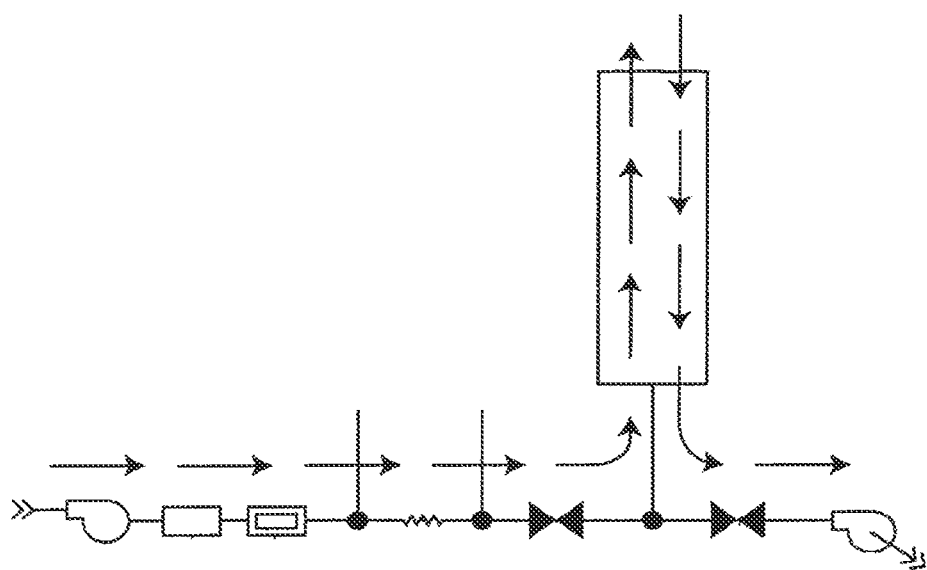
FIG. 6 depicts one pneumatic handler suitable for high quality breath gas measurements.
Figure 7:
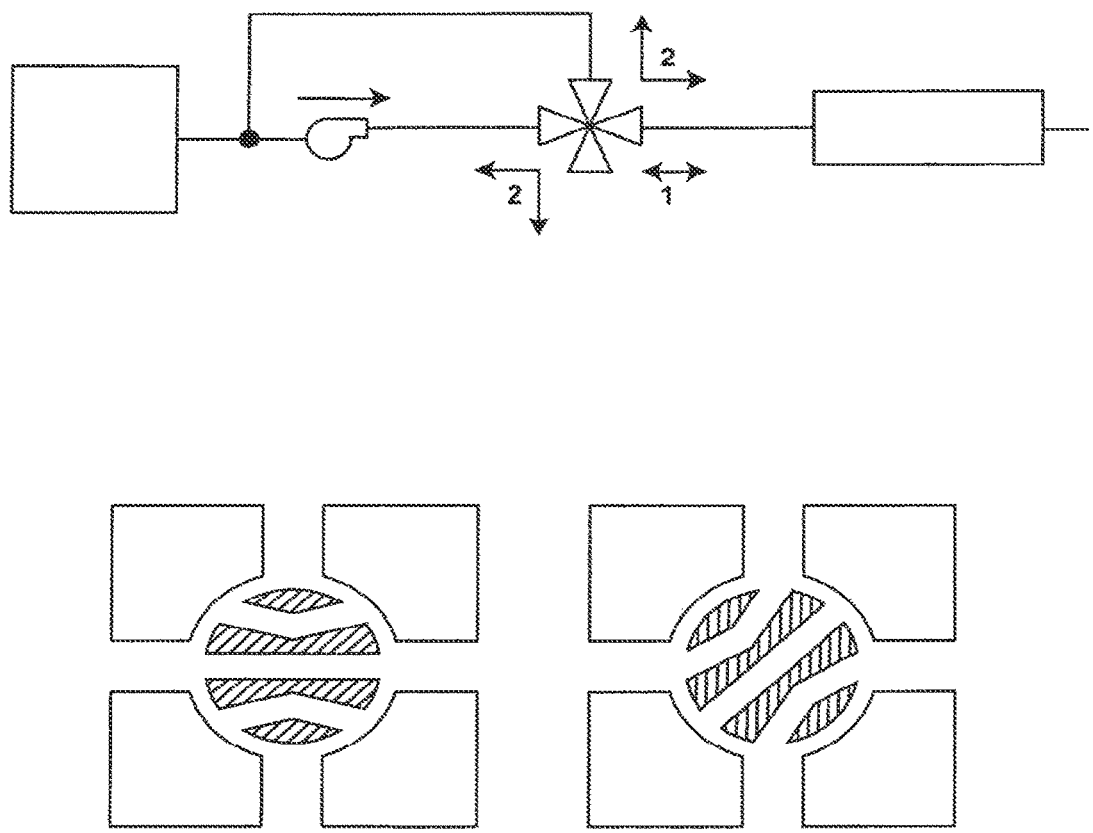
FIG. 7 shows one approach to component reduction using a specialized ball valve.
Figure 8:
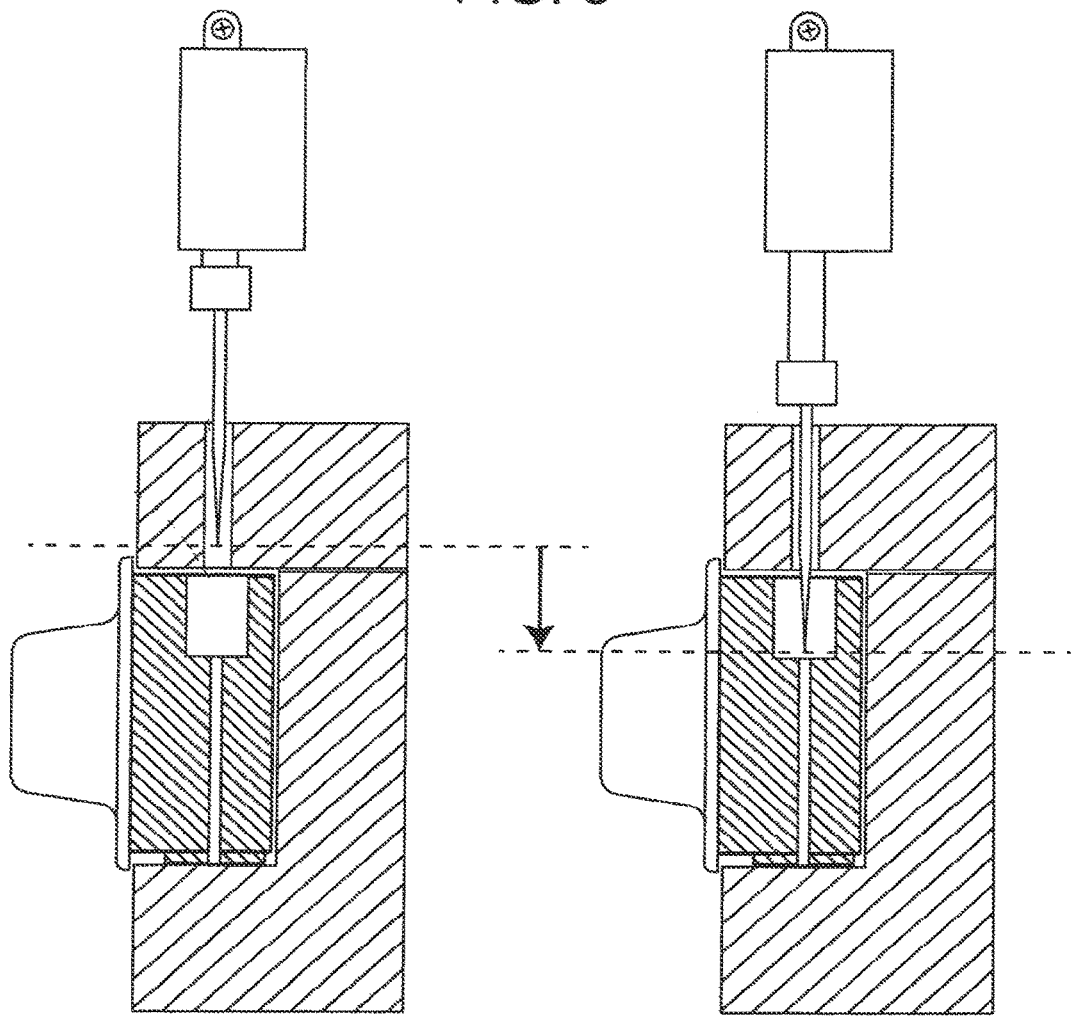
FIG. 8 shows an exemplary reaction initiator based on a needle.

FIG. 4 and FIG. 5 depict optical configuration embodiments useful for endogenous breath sensing. FIG. 4 depicts a general layout for an optical sensing subsystem configuration comprising a camera (36) in relation to a light source (38) and cartridge (40). FIG. 5 depicts similar components from a top-view, illustrating the relative angle of the excitation source (42) to the incident plane of the cartridge (44) and to the focal plane of the camera (46). Such an embodiment reduces glare from the excitation source and is suitable for capturing high-quality images of the sensor chemistry. The images can be processed to derive or to interpolate from correlations of analyte breath concentrations and developed color. A camera is especially well-suited to base systems where multiple chemistries are to be detected due to the additional power afforded by both a wide spectral range, a degree of spectral sensitivity (images are captured onto red, green, and blue pixels), and a high degree of spatial resolution. In particular, spatial resolution allows very simple instrumentation setups to be used for a wide range of applications, for example quality assurance. Other embodiments such as semiconductor photodetectors can provide low processor overhead and compact size.

In accordance with an aspect of the present invention, a cartridge is provided for use in carrying out various methods according to the invention. The cartridge optionally but preferably forms a separate component from the remainder of the breath analysis device, and comprises reactants or consumables used by the various tests or analyses. Again, optionally but preferably, the cartridge is configured so that, when disposed in its "inserted" position in the breath analysis device, it forms a substantially light-tight seal so that ambient light or like radiation that may adversely impact features of the methods such as the colorimetric analyses are avoided.

Cartridges according to presently preferred embodiments in the context of the present inventions include at least one "packed bed" reaction zone or cavity, which reaction zone or cavity may contain the one or more reactants as described herein below. Such cartridges also may comprise breath conditioning means, such as a flow controller or pressure regulator, a desiccant (e.g., calcium chloride), a temperature controller, and the like. The cartridge also may comprise a cavity or portion for containing a "developer solution" or like fluid to facilitate the analysis, e.g., as described more fully herein below. In some preferred embodiments, each cavity is separated from the others by a porous retention medium. One example is a porous polyethylene disk.

Preferred cartridges comprise reactive chemistry capable of reacting with at least one breath analyte, and preferably at least one endogenous breath analyte. There are a variety of cartridge configurations that can work with systems according to the invention for measuring at least one analyte, preferably an endogenous analyte, in breath.

In one embodiment, cartridges comprise an encasement that has a flow path for breath that is further coupled to an automated reaction initiator that allows the developer solution to contact the reactive chemistry. Cartridges preferably contain a porous media located adjacent to the reactive chemistry. The cartridge may contain a single reactive chemistry or a plurality of reactive chemistries.

In another embodiment, cartridges contain a pneumatic loader that transports developer solution through the cartridge.

In yet another embodiment and aspect of the invention, cartridges block ambient light when inserted into the base unit and preferably comprise a handle. As noted herein above, where internal system components such as the interactants, intermediate products, etc. are light-sensitive, the base may comprise an exterior surface that forms an interior and shields the interior from ambient light, wherein the exterior surface comprises an aperture; and the cartridge may comprises a shroud that substantially conforms to the aperture to shield ambient light from entering the aperture when the cartridge is coupled to the base.

Cartridges can be designed into various shapes and sizes to facilitate different applications. In one embodiment, the cartridge is comprised of: (a) reactive chemistry, (b) a first chamber containing a first developer, and (c) a second chamber containing a second developer. The first and second developer can be the same or different. In another embodiment, the cartridge is comprised of: (a) reactive chemistry, (b) a chamber containing a developer, and either (c) mechanism for coupling the cartridge to a pneumatic loader or remover, or (d) mechanism for coupling to a reaction initiator. In a preferred embodiment, the cartridge requires no external liquid flow to the cartridge.

Figure 13:
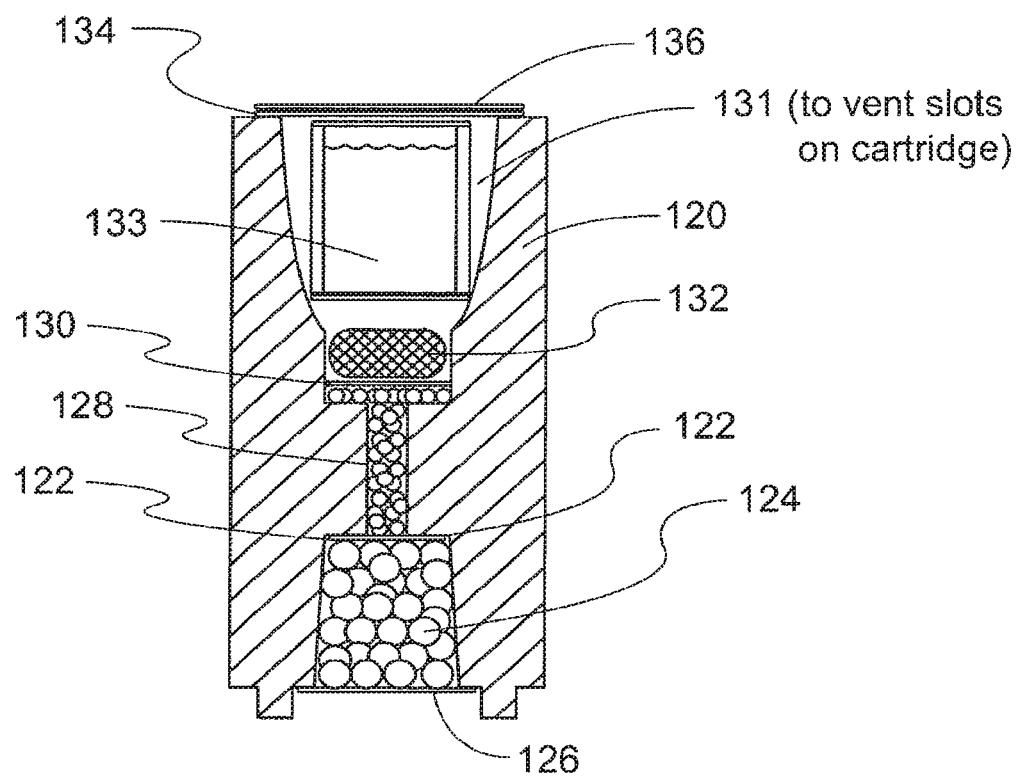
FIG. 13 shows an exemplary general schematic of cartridge design.

An exemplary general schematic of cartridge design is shown in FIG. 13. This cartridge is preferably used for optical detection, and preferably includes reactive chemistry that can be used to detect endogenously produced analytes in human breath. Here, the reactive chemistry (128) is contained within a cartridge housing (120) consisting of a single piece. Preferably, but not necessarily, the housing is comprised of material that is optically clear. There is a membrane (122) that separates the reactive chemistry from a breath conditioner (124). In this embodiment, the breath conditioner (124) is a desiccant, but this may also be a scrubber or pre-concentrator. The breath conditioner is kept tightly packed by a porous membrane (126). In some embodiments, a peelable or piercable barrier material can be affixed to the underside of the cartridge to enhance storage of the reactive chemistries and breath conditioners. On the other side of the reactive chemistry is a retainer (130). The retainer serves to keep the reactive chemistry tightly packed. This retainer can be molded compression fittings, on-cartridge gaskets, o-rings, etc. Atop this retainer is a porous media (132). The porous media is designed to allow liquid developer solution (133) to flow towards the reactive chemistry. In an alternative embodiment, components (130) and (132) are replaced by a single component that can be both compressive fit into the packing pocket and porous. Hydrophilic, porous polyethylene disks are useful for this purpose. Developer solution is contained within a breakable ampoule (133) that sits within a receptacle in the upper portion of the cartridge housing (131), which is formed with vertical channels to facilitate venting of air when developer solution flows down into the channel filled with reactive chemistries (128). The ampoule-containing receptacle (131) is sealed with a piercable membrane (134). Once the cartridge is inserted in the base unit, the piercable membrane and the piercable container are pierced by the reaction initiator of the base unit so that liquid flows to the reactive chemistry. To ensure that residual liquid does not leak out post-use of the cartridge, there is a rubber septum (136) that seals the cartridge. The cartridge preferably is designed such that the developer solution is "absorbed" by the reactive chemistry and/or conditioner (e.g., desiccant) such that it does not leak through the bottom of the cartridge. One optional addition is coupling to a pneumatic loader or remover (not shown). This pneumatic loader/remover acts as a pump and pulls/pushes the developer solution through the cartridge. Thus, while the cartridge can be oriented such that the liquid interacts with the reactive chemistry due to gravitational pull or wicking, it can also be designed to allow for automated, active interaction via a pneumatic loader/remover.

Figure 14:
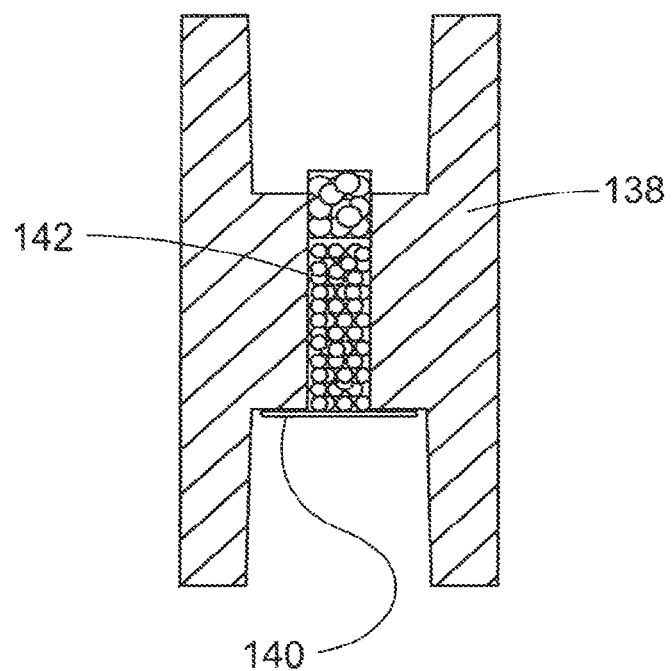
FIG. 14 shows one alternative to the retainer (130) of FIG. 13 for containing reactive particles.

FIG. 14 shows one alternative to the retainer (130) of FIG. 13 for containing reactive particles (128). A plastic cartridge (138) forms the main housing for a packed bed of reactive materials (142). A permeable retainer (140) is affixed on the underside of the column as discussed elsewhere. A porous material, for example plastic, metal, ceramic; or fibers such as glass or metal wool is compression fit into the channel. The porous plug is pressed tightly against the packed materials (142) to prevent shifting during usage or transportation.

Figure 12:
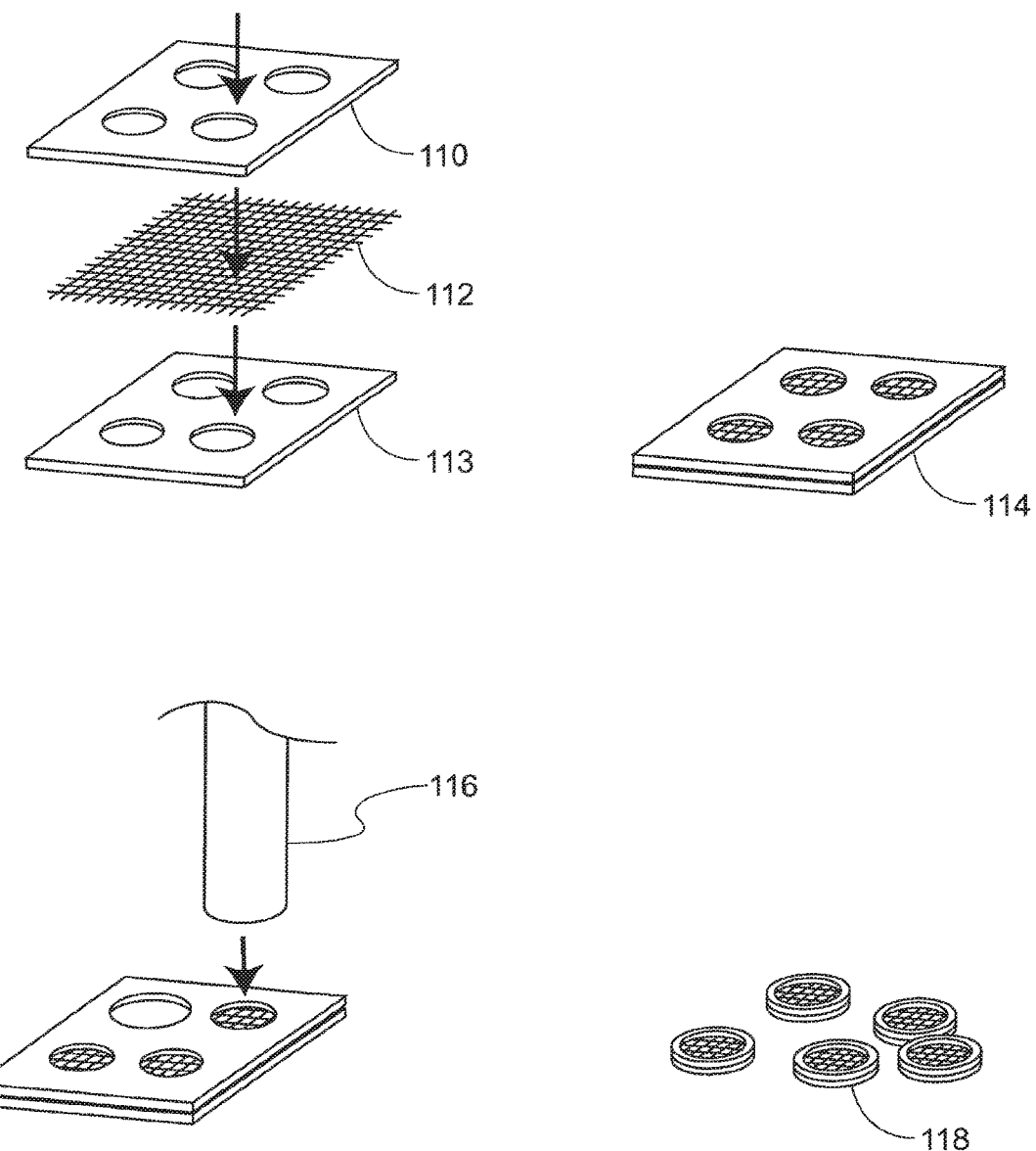
FIG. 12 displays an example of a substrate sheet that can be pressed into retention disks.

The porous seal (130) exemplified in FIG. 13 is preferably comprised of a material with the following properties: fine pore (able to retain small particles, for example 75 micron particles), high open area (low pressure drop, low resistance to flow), inert to analyte of interest, amenable to pick and place automation, able to adhere sufficiently to the substrate. Materials in sheet form are often amenable to mass production. Sheets of various substrates are easily pressed into laminates. A sheet that is porous to begin with is easily processed into retention disks. FIG. 12 displays an example of a substrate sheet that can be pressed into retention disks. A sheet of thin polyimide (0.001"- 0.003") with adhesive backing is punched with an array of holes (110, 113) (for example Devinall SP200 Polyimide film with FastelFilm 15066 adhesive backing). A sheet of fine woven nylon mesh (112) (307×307 mesh, 9318T48 from McMaster-Carr) is pressed into a laminate (114) with the punched polyimide. The laminate is then punched with a larger diameter tool (116) to create laminated disks with a porous center (118). The outer region contains a topside annulus of polyimide. Such disks are easily picked up by vacuum means to be positioned easily, even into deep recesses. Disks are adhered to receiving surfaces using heat pressing tools. The particular adhesive melts at 66 C, well below the melting points of numerous plastics suitable as cartridge wall materials. Disks can be fashioned by this method using commercial rotary cutters and other common production tools. These disks are especially well-suited to retaining reactive media in deep wells, for example (324) in FIG. 26, discussed infra.

Foils and numerous other plastics are also available with adhesive backing. Polyimide top layers can be preferable to foil layers in some attachment methods since foil layers can have a greater tendency to separate from their adhesive backing during certain heat pressing processes, especially where the contact surface area is large. Polyimide may be preferable to other plastics due to its potentially high heat transfer and resistance to heat damage, especially when thermal grade polyimides are used.

Figure 15:
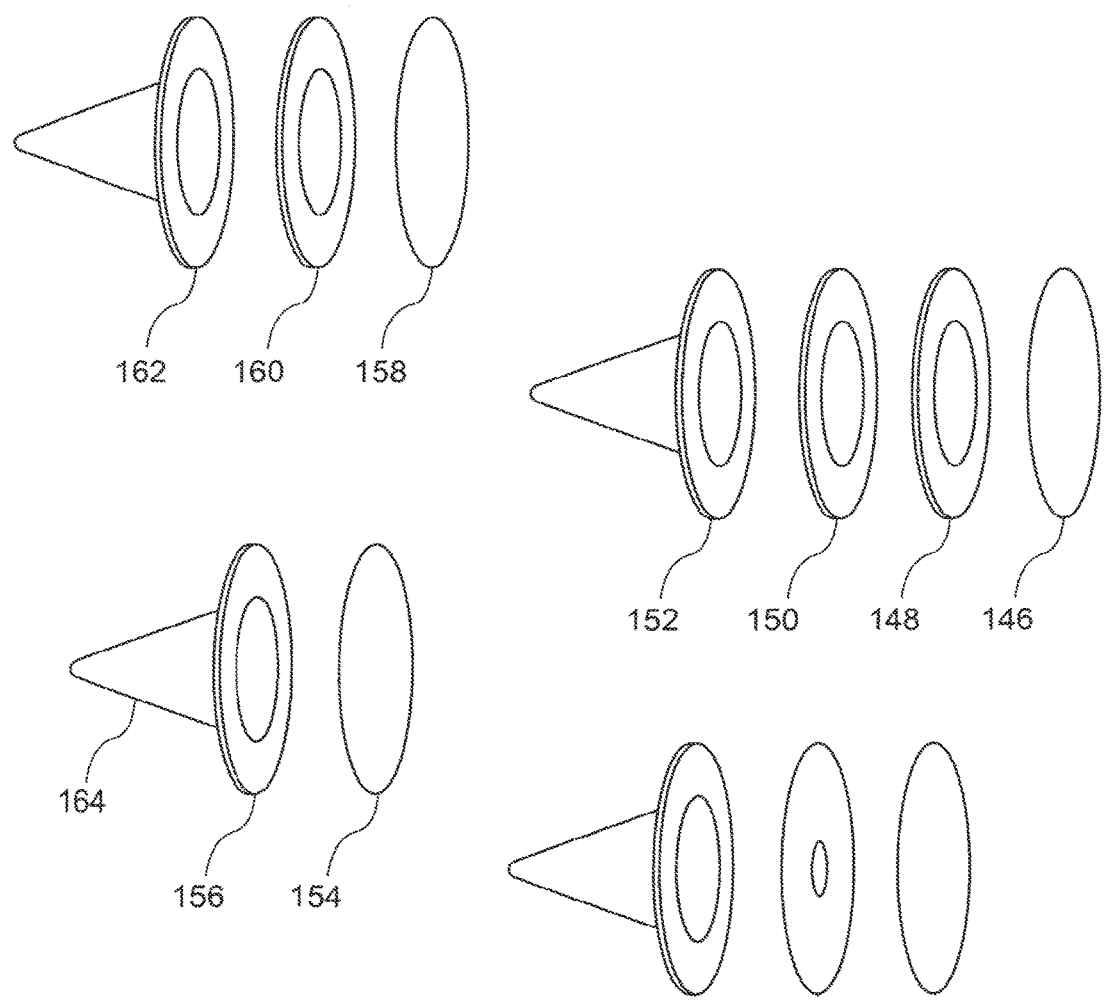
FIG. 15 shows four embodiments of a piercable foil ampoule.

Liquids can be contained in the pockets of cartridges, using the cartridge material as side walls with foil or other membrane barriers adhered to the cartridge surfaces. For aggressive solvents, for example dimethylsulfoxide or methanol, such solutions may be temporary due to solvent attack of the adhesives. One embodiment of the present invention uses a separate part to contain the liquid reagent. This allows complete materials control of liquid contact (the walls of the cartridge do not need to be a materials concern as far as solvent interaction is concerned). Various "cans" of liquid can be configured, and these cans can be dropped into an open pocket in the top piece of a cartridge. Preferably a liquid can or ampoule is completely inert to the retained liquid. FIG. 15 shows four embodiments of a piercable foil ampoule, described in the following paragraphs.

Breakable solvent ampoules can be manufactured by a variety of methods. For example, in one case, a flanged conical foil base (152) is welded or otherwise adhered to a weldable or heat-sealable intermediate material (150) to form the bottom half of a clamshell. A top foil layer (146) is likewise attached to a weldable or heat-sealable intermediate material (148) to form the top half of the clamshell. The bottom half is then filled with volatile liquids and the top half ultrasonically welded or heat sealed to the bottom half. The volatile liquid is contained within up to four barriers: the foil material forming the major contact surface, the weldable/sealable intermediate material (for example low thermal conductivity thermoplastic), the weld joint between the foil and the plastic (adhesive), the weld joint between the weldable intermediate materials (low thermal conductivity thermoplastic). This configuration is useful because (a) it allows an adhesive time to cure independent of solvent presence (the adhesives can be fully cured before filling of the solvent), thus enabling a wide range of adhesives to be employed; (b) conductive heating caused by ultrasonic welding is shielded by low thermal conductivity thermoplastic, eliminating or controlling the amount of fill solvent lost to evaporation during ultrasonic welding.

A thermal barrier material is another example of a breakable solvent ampoule. A second case ultrasonically welds the two foil half clamshells to one another, using a bottom half insert material as a thermal barrier. That is, a top foil (154) is attached to the bottom foil (156) by direct ultrasonic welding of the metal foil. The solvent is pre-loaded for welding, thermally protected by a thermal barrier, such as a hollowed out wax cone (164). The thermal barrier must protect the solvent from conductive heating caused during ultrasonic welding, but it must also be easily pierced. Other materials, such as thin plastics, rubber, or spray-on silicone adhesives may also be suitable.

An adaptation of the thermal barrier method is to perform ultrasonic welding in the presence of appropriate heat sinking. The ultrasonic weld jig contains an annular clamp made of highly conductive metal. The clamp engages the top and bottom metal foils inward from the outer locations of ultrasonic welding such that any heat conducting away from the weld joint sinks into the conductive clamp. Alternative methods of heat sinking, such as blowing the bottom foil with cold air may also be suitable, depending on the solvent in use.

A third method for solvent encapsulation relies on a crimp seal between a top foil (158) and a bottom foil (162). A wax gasket or gasket comprised of solvent-resistant material (160) is included between the layers to increase the retention time of the volatile liquid into the ampoule. The gasket material must be chosen with the appropriate resilience and barrier properties to the solvent of interest.

Ampoules can also be blow-molded from numerous materials including glasses and plastics. These single-material ampoules are constructed of thin walls to enable ampoule piercing, but sufficiently thick walls to obtain the necessary barrier properties.

Metals are excellent as barrier materials and can be sealed in gas-tight fashion through crimping (such as a beverage can). Miniature ampoules made of aluminum and other metals can be manufactured and dropped into the head portions of disposable cartridges.

Figure 16:
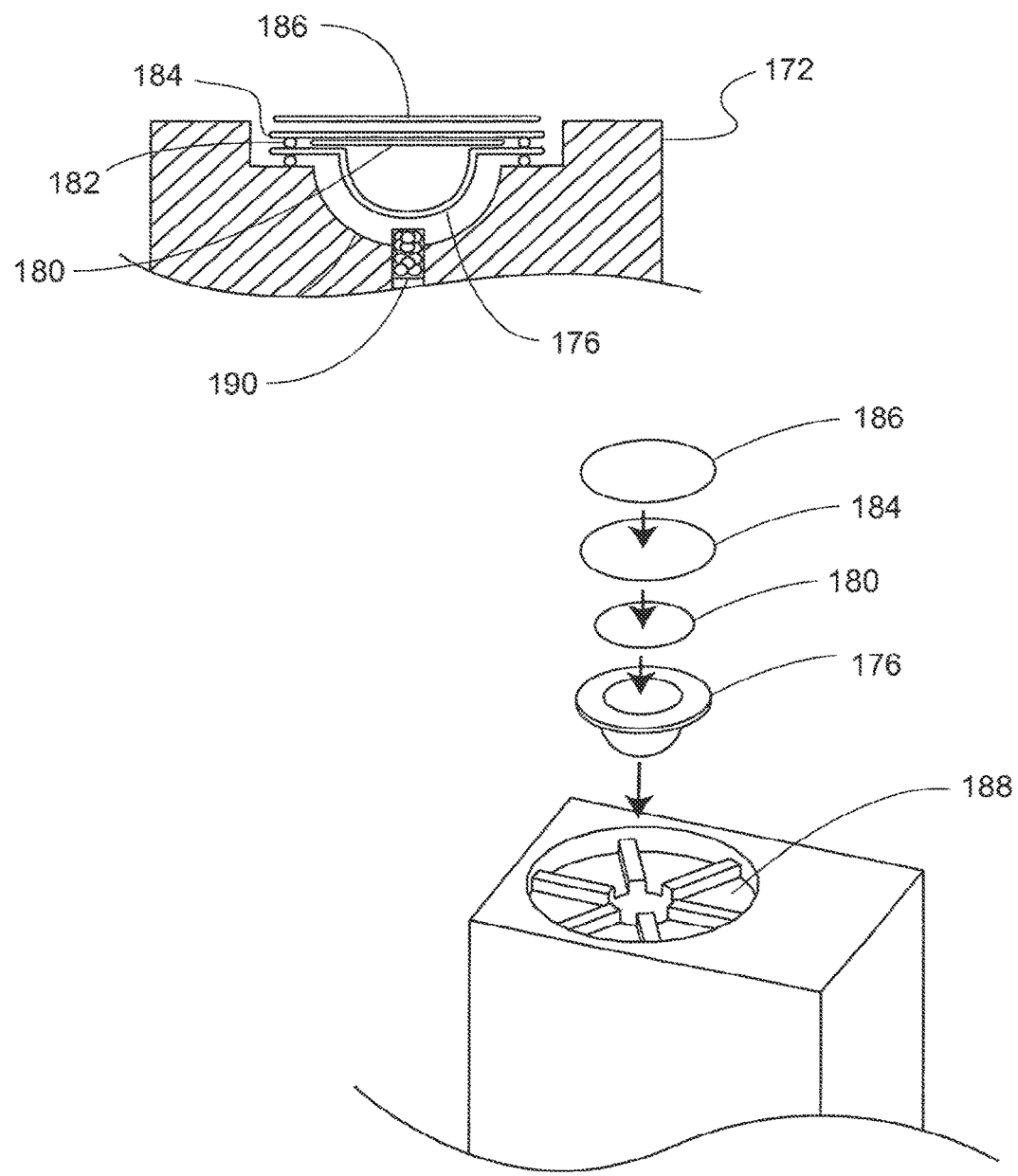
FIG. 16 shows certain embodiments of a piercable ampoule.

FIG. 16 shows certain embodiments of a piercable ampoule. In this embodiment, a cold-formed foil (176), or other formed, piercable barrier material, is attached into the head portion of a base plastic carrier (172) using points of adhesive. These points may make contact with a series of bosses (188) and are intended to adhere the floor of the ampoule to the base plastic carrier in a non-airtight fashion. The floor of the ampoule (176) is filled with solution, and a temporary barrier (180) may be affixed to seal the liquid. The temporary barrier can be affixed through pressure sensitive adhesives, thermally set adhesives, or any other convenient method. The adhesive for the temporary barrier does not need to resist and retain the solution beyond the time required to complete the sealing process. A circular bead of adhesive (182) is next applied. This adhesive forms a permanent barrier for the entrapped solution, but a temporary barrier (180) allows the permanent barrier material (182) to cure independent of solution activity. The liquid is capped with a disc of barrier material (184). A separate material (186), such as a rubber septum, is optionally placed to prevent temporary passage of liquid after the barriers have been broken.

This method can be used to retain particles in a packed state. That is, by positioning of a compressible, porous material (190) directly beneath the bottom floor (176), particles can be immobilized.

Figure 17:
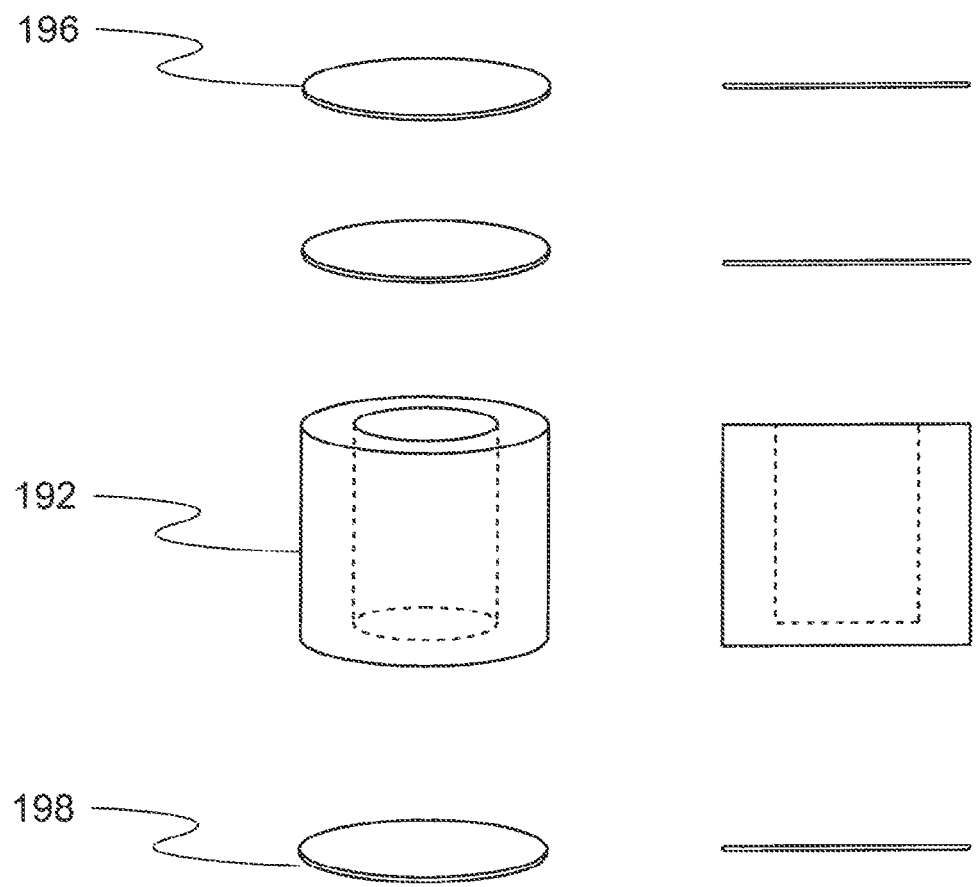
FIG. 17 shows embodiments of a piercable can.

FIG. 17 shows embodiments of a piercable can. In this example, a thin-bottomed can (192) is cast of a thermoplastic material. After filling with the desired liquid, a thin barrier material (a laminated foil with a thermoplastic layer, for example) can be attached via an appropriate method, such as ultrasonic welding or heat-sealing. As necessary, more extensive barrier materials (196, 198) can be affixed after the can is filled with liquid. Optionally, depending on the material requirements of the liquid to be contained, barrier materials (196, 198) can be attached directly to the can through pressure sensitive adhesives, thermally set adhesives, or other methods (note that the can does not need to be constructed of thermoplastic materials). A variation on this design uses a thick-walled plastic cylinder as the body of the ampoule and is sealed on both ends with piercable barrier materials.

Single analyte cartridges can be configured in numerous ways to facilitate various chemical reactions. Sequential columns of dry reagents can be packed into stacked columns (where shifting of particles is not a concern) or into partitioned pockets within the device. Some examples are shown in FIG. 18 and FIG. 19.

Figure 18:
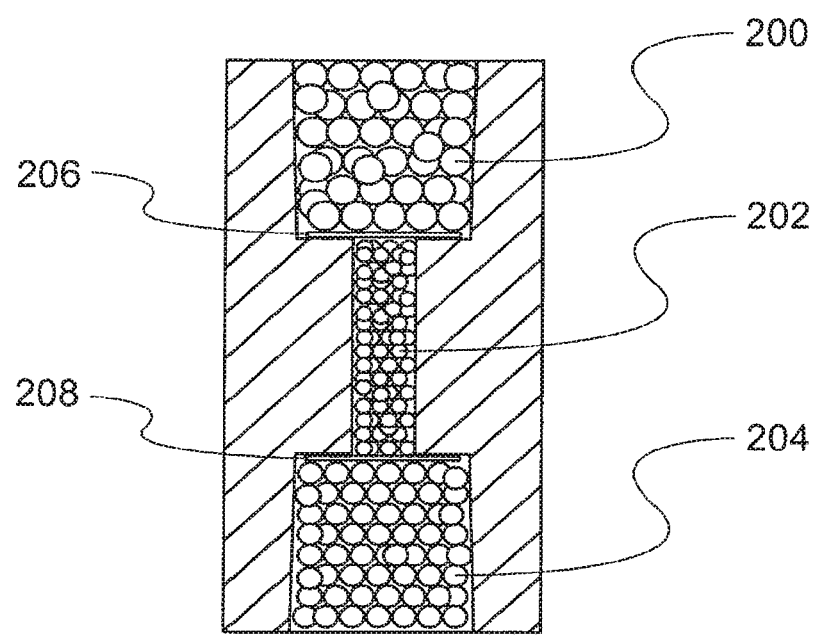
FIG. 18 shows different dry reagents packed into a single column.

In FIG. 18, three distinct dry reagents (200, 202, 204) are packed into a single column. Porous membranes (206) and (208) are in place to retain the reagents. Reagents can be of dissimilar size when membranes are in place. Additional reagents can be packed using increasing diameter sections, such that flat ledges are created whereupon retention means can be affixed.

Figure 19:
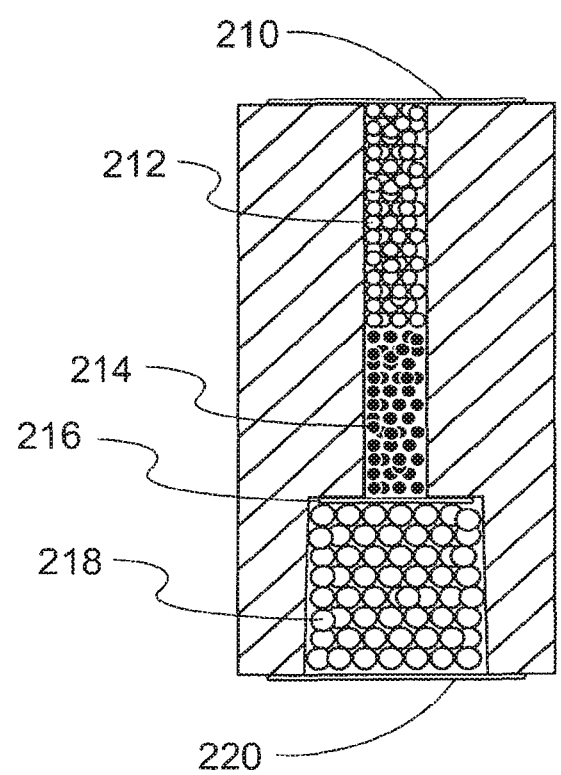
FIG. 19 shows another set of stacked dry reagents packed into a single column.
Figure 20:
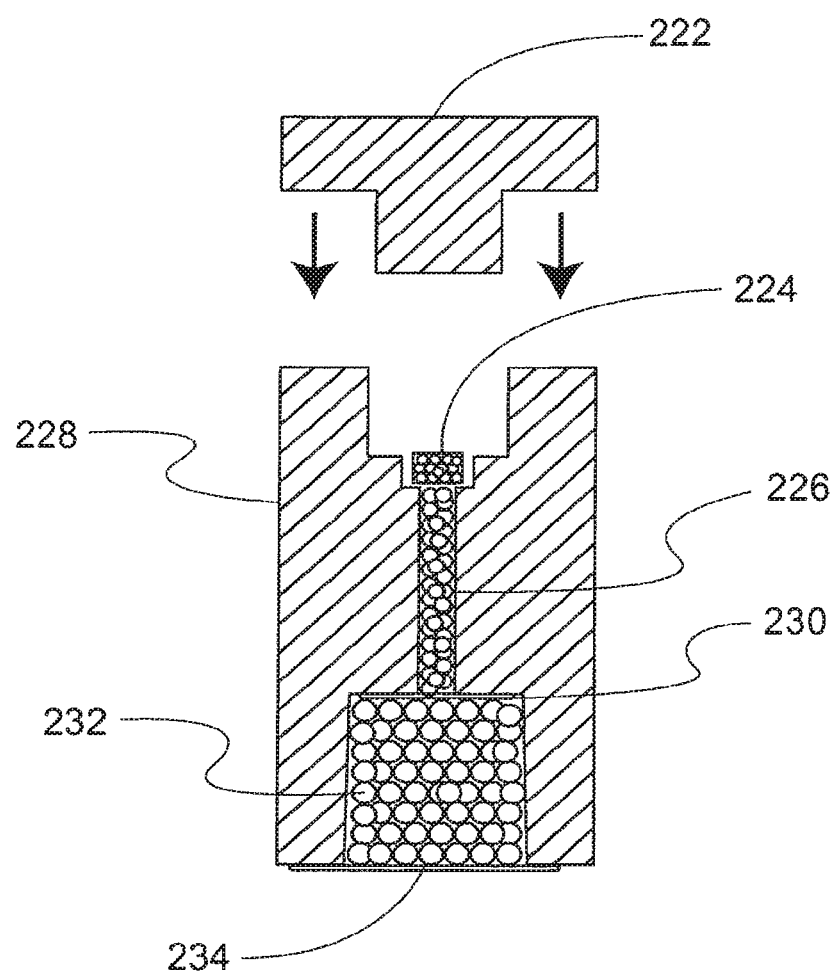
FIG. 20 illustrates reagents being held in place using compressible, porous media.

In FIG. 19, reagent stacking is shown. When distinct reagents of similar size (212 and 214) need to be immobilized, they can be packed into a single column as shown. Larger particulates (218) will need means of separation and retention (216). One method of separation makes use of thin disks of porous material, such as nylon mesh as described in FIG. 12, but porous plastics or other porous media can be used in additional embodiments. The outer ends can be sealed using retention membranes (210) and (220). It is often desirable to pack columns with reagents in such a manner that the reagents are not free to move. In this case, materials can be held using compressible, porous media. FIG. 20 illustrates such a configuration. In this illustration, a cartridge is comprised of two pieces, a top (222) and a base (228). A first dry reagent (232) is packed into the lowermost pocket of the base, retained by two porous membranes (230 and 234). A second dry reagent (226) is packed into the central column of the cartridge. At the topmost end of the central column, a wider bore (224) has been molded to accommodate slight overfilling of the dry reagent (to relax filling tolerances) and to facilitate compression of the reagents with a porous, compressible material. This material, when compressed by the top (222), still allows fluidic communication through the top and bottom pieces while compressing the dry reagents 226) to keep them immobile.

Figure 21:
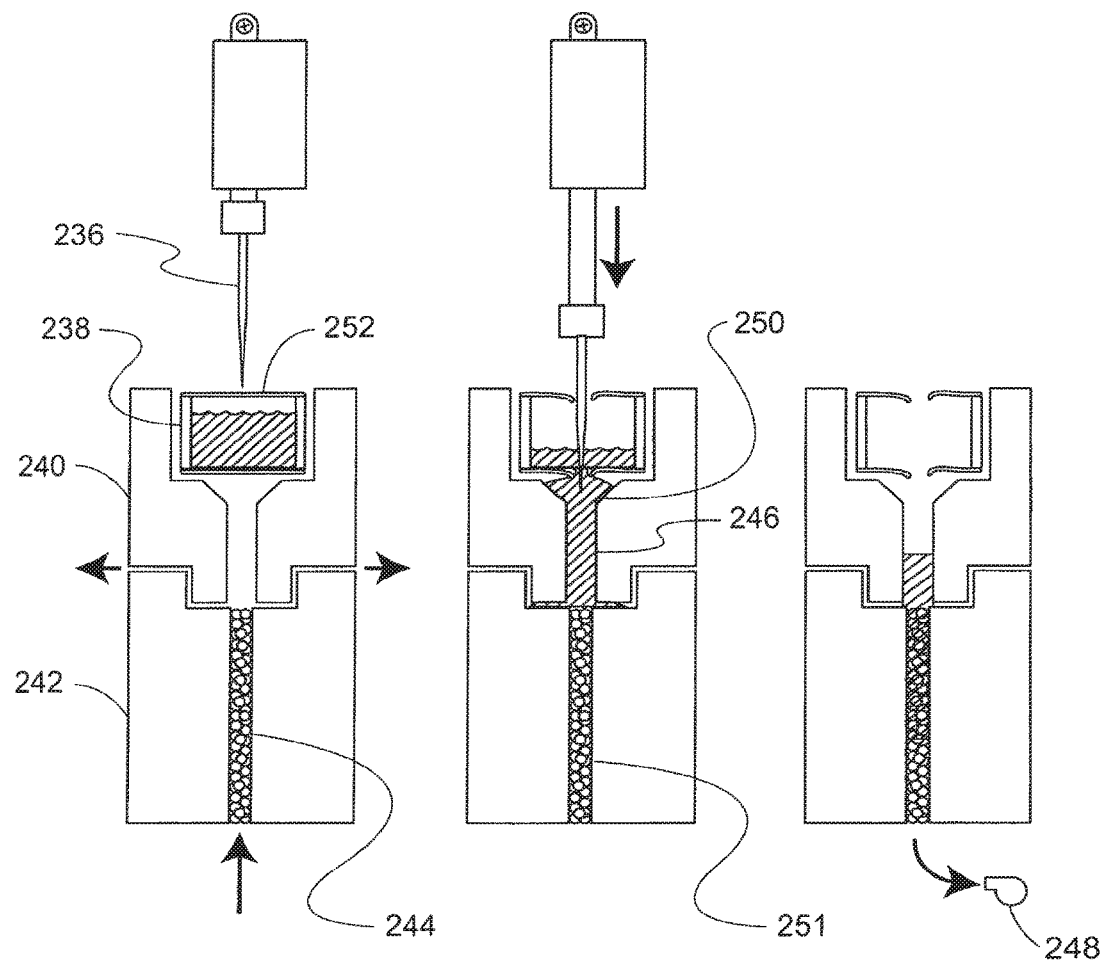
FIG. 21 shows an example of how a liquid reagent can be immobilized onto a cartridge and how it can be released at the time of reaction.

Liquid reagents can be packed into sensor cartridges to facilitate numerous chemical reactions useful in breath analysis. FIG. 21 shows an example of how a liquid reagent can be immobilized onto a cartridge and how it can be released at the time of reaction. In a top piece of a cartridge (240), a containment means (238) is provided for the liquid reagent. This can be a distinct component (238) that is dropped into a pocket in the top piece (240) or it can be integral to the top piece. In any case, this reagent ampoule (238) can contain liquid reagent between two piercable membranes (252) that are impermeable or otherwise amenable to the reagent of interest. A needle (236), solid or hollow, is pressed through the membranes at the required time, causing the liquid reagent to flow through a conical cutout (250) in the cartridge and through a downcoming channel (246) toward the reactive bed (244). In this configuration, the seal between the top piece (240) and base piece (242) is not airtight (to allow gas flow from the bottom of the reactive bed (244) through to the top and out the sides). Thus, the liquid reagent is preferably of low viscosity and appropriate surface tension such that the liquid drops all the way to the top of the reactive bed and is drawn into the reactive bed when a suction pump (248) is activated.

Figure 22:
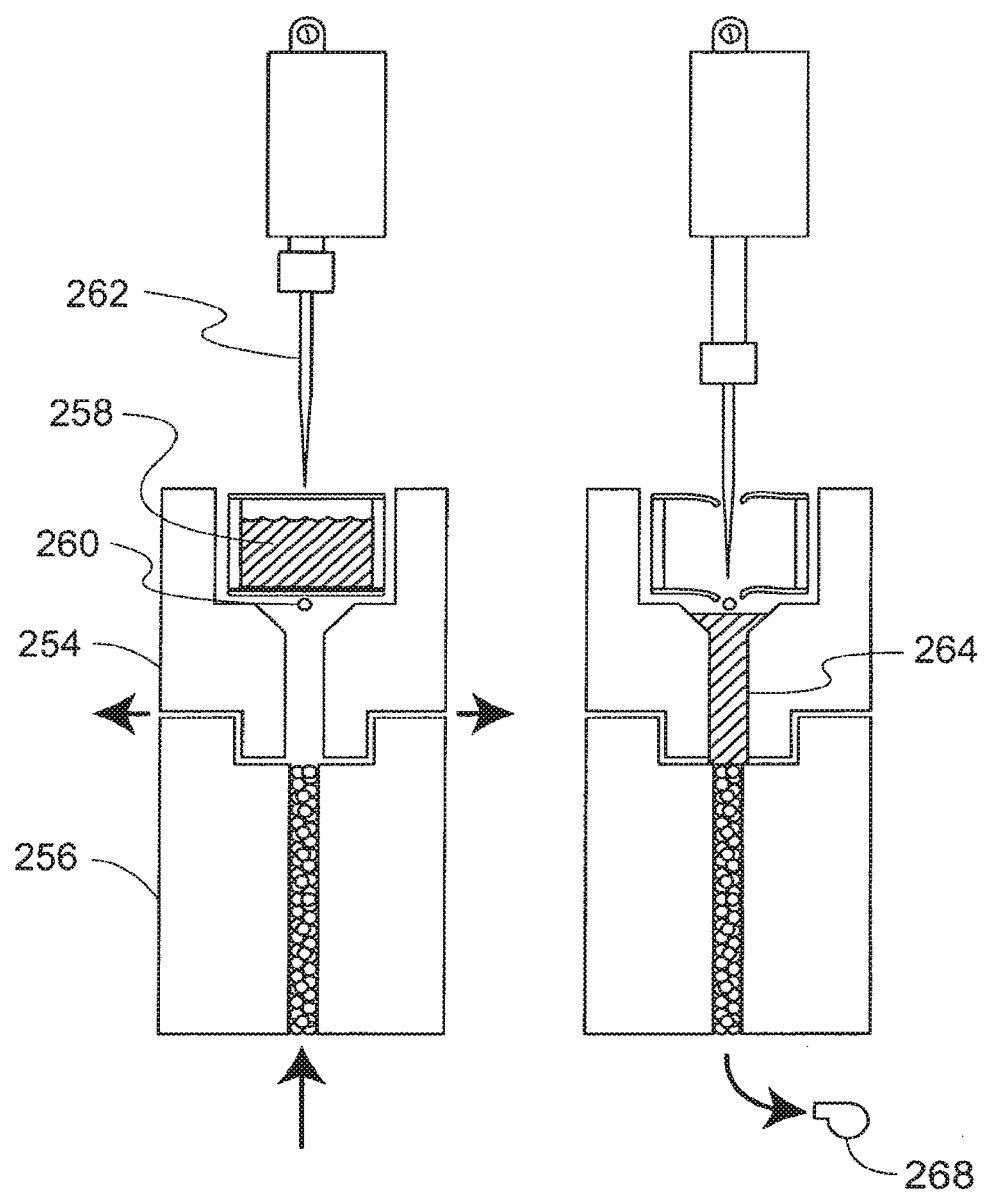
FIG. 22 demonstrates another embodiment of how a liquid reagent can be immobilized onto a cartridge and how it can be released at the time of reaction.

FIG. 22 provides another embodiment. In this alternate configuration, a hole (260) is cut into the top piece so as to provide a gas exit port when the top piece (254) and the bottom piece (256) are fastened with an airtight seal. In this case, gas is flown over the reactive bed and out the exit port (260). Next, a pin (262) is pressed through a top and then bottom barrier to free the contained liquid (258) and to create a hole to allow gas to fill the vacated space. The liquid fills a downcoming channel (264), blocking the exit port and creating a liquid seal so that a suction pump (268) can pull the liquid through the channel and through the reactive bed.

Figure 23:
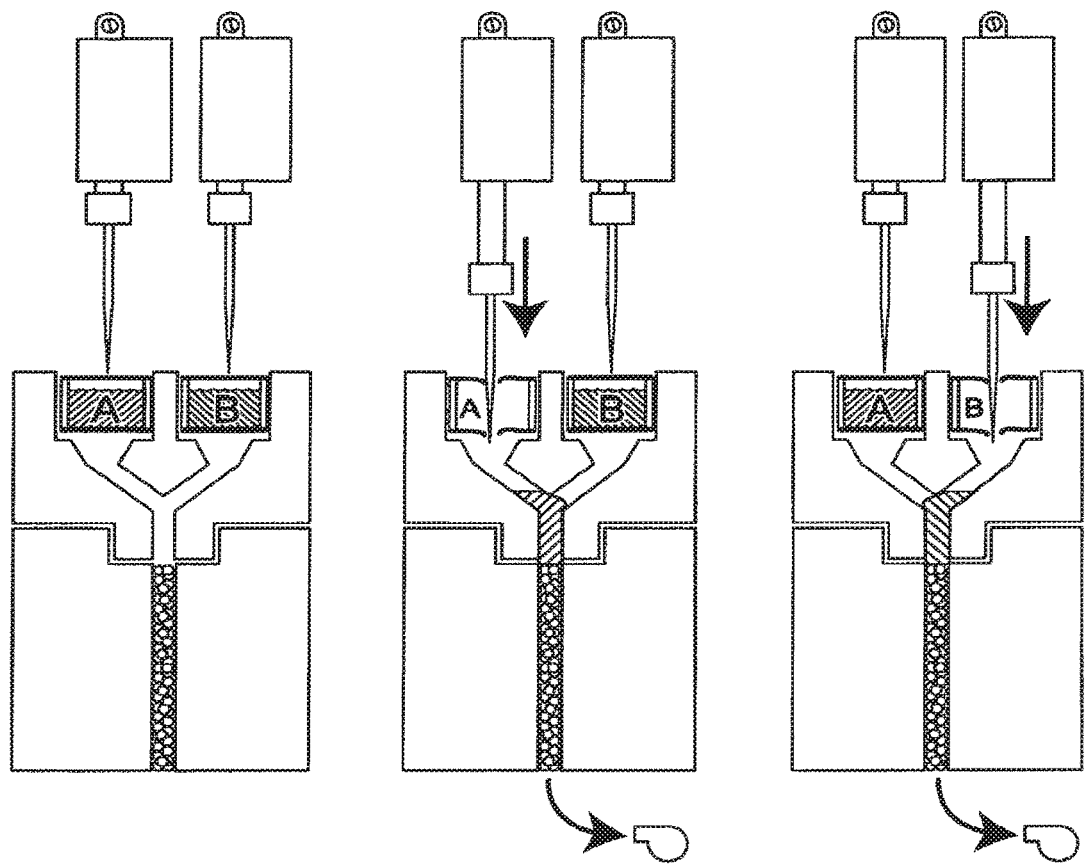
FIG. 23 illustrates an example of a multi-liquid cartridge.
Figure 24:
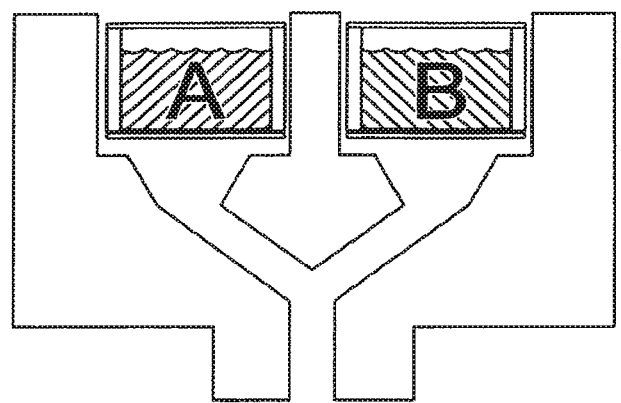
FIG. 24 illustrates another example of a multi-liquid cartridge.
Figure 24:
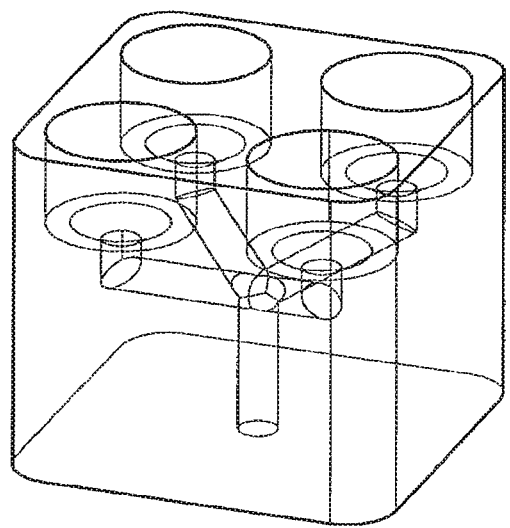

An extension of the liquid containment/release mechanism as described above allows multiple liquid reagents to be integrated into a single cartridge. FIG. 23 and FIG. 24 illustrate examples of a multi-liquid cartridge. In FIG. 23, two reagent wells A and B contain two reagents (or one reagent, if desired) between breakable seals as discussed. The downcoming channels are merged into a single line. When the first seal is broken, liquid from A fills the downcoming channel as before, where it is then suctioned away by a connected pump. Next, the seals containing liquid B are broken, and the same procedure is followed. FIG. 24 shows a top piece that contains four such containers of liquid. This method allows very sophisticated fluidic handling to be done with reagents that are located on a single disposable piece.

Although chemical reagents may be consumed with each reaction, cartridges of the present invention need not be limited to single-use. Multiple use devices can be comprised of strips or carousel wheels of devices in a single substrate. This same form factor can be used to allow multiple analytes to be measured in a single breath sample, either with sequential or parallel processing.

Figure 25:
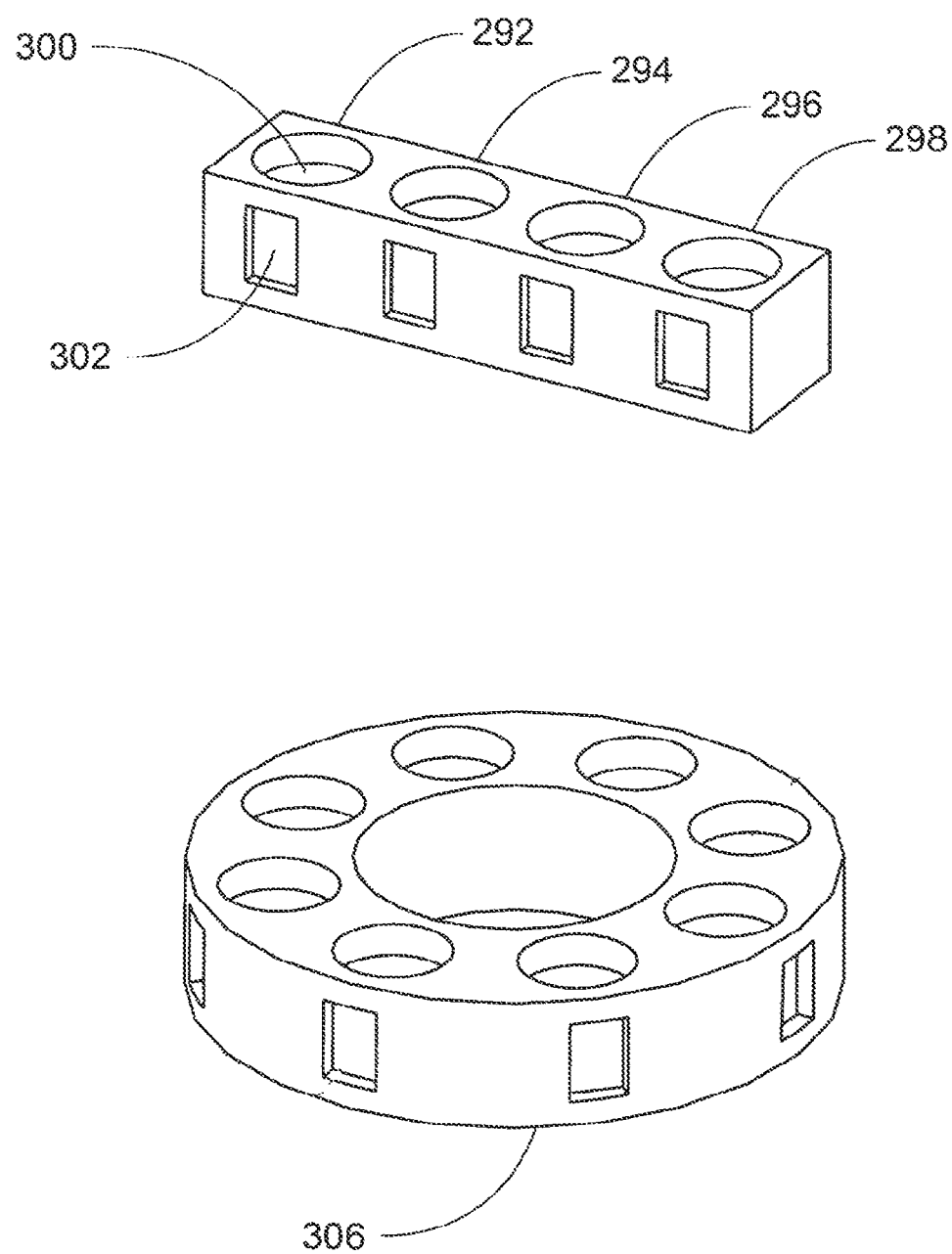
FIG. 25 shows some cartridge designs that enable multi-use applications.

FIG. 25 shows some cartridge designs to enable these applications. Displayed on the left side of the diagram is a strip or blister pack of reactive channels. Each of the four channels (292, 294, 296, 298) depicted can be filled with identical or different reagents, depending on whether the application is to measure, as examples, acetone on four occasions, acetone and ammonia each on two occasions, or to measure 4 separate analytes from a single sample. Each channel can be sealed with a separate foil barrier (300) or with a single foil strip placed over the entire top portion. Windows (302) to reduce material volume and wall thickness for optical clarity can be fashioned next to each packed column. The base device must contain four fixed channels or moving parts (to move either actuators or the table containing the multi-channel cartridge). Also shown in FIG. 25, multiple channels are incorporated into a carousel-type device (306) which rotates to align each channel with a fixed-position seal breaking/fluid driving head.

Figure 26:
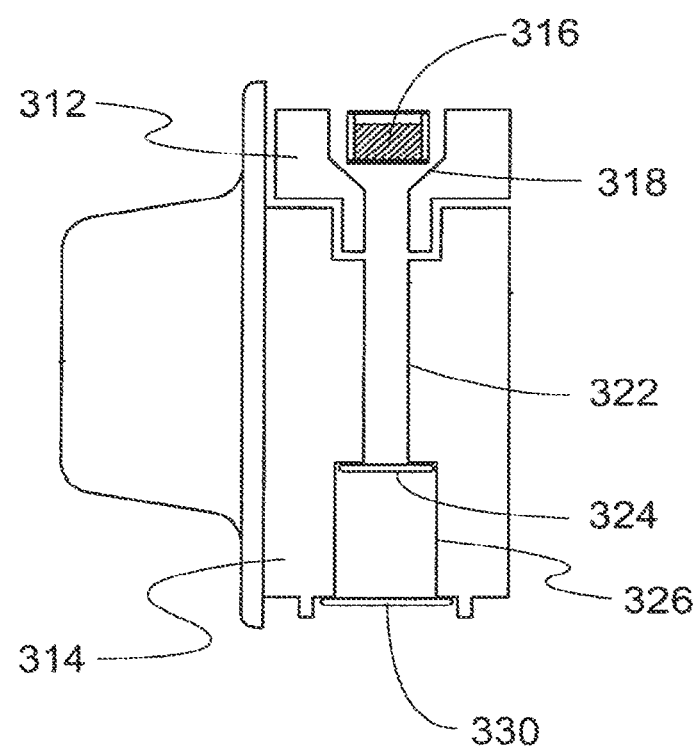
FIG. 26 shows an embodiment of a cartridge design.

FIG. 26 shows an embodiment of a cartridge design that facilitates or accomplishes the following tasks: (a) sample desiccation, (b) sample concentration, (c) sample reaction, (d) built-in fluid direction control (via one non-reversible one-way valve, schematically similar to three one-way valves), (e) two-phase reagent containment (solid reactive chemistry, liquid developer). (f) inexpensive reagent interfaces (retention means), (g) easy insertion into base device, and (h) low reagent volume.

The exemplary cartridge in FIG. 26, in connection with appropriate reagents, is appropriate to measure acetone in human breath. The cartridge is comprised of two pieces that are mechanically fastened together, for example with snap fits. A top piece (312) attaches to a base piece (314). The top piece and base piece, by design, do not form an air-tight seal. Liquid reagent is contained in a pocket (316) in the top piece. One embodiment consists of a developer solution contained between two foil seals, one on the top plane of the pocket and a second on the bottom plane. Beneath the bottom foil seal, a conical pocket (318) is fashioned to facilitate liquid reagent dropping without intermittent air bubble entrapment. Reactive chemistry is packed into a column (322) running through the center of the base piece. To ease tolerances on reactive chemistry packing, the top-most portion of the reactive column is widened. A porous, compressible medium is deposited in the top-most, widened column portion such that when the top piece (312) is sealed against the base piece (314), the reactive material loaded into the column (322) is packed tightly. In general, open cell foams, both foam-in-place and pre-formed and cut, are well-suited as porous, compressible retention barriers as long as the chemistry is compatible with the system. Columns that are not packed tightly are subject to material shifting, a situation which hampers reproducibility and increases measurement errors. Desiccant materials are packed into a lower, wider column (326). A porous seal (324) is attached to the ceiling of (326) to provide a gas-permissive retention mechanism for the reactive material. In one embodiment, woven nylon mesh provides this means while incurring negligible resistance to gas flow. A similar barrier (330) forms the floor of (326). The base of the cartridge is formed to facilitate compression against a trapped gasket in the base device to enable leak-free communication with the gas delivery plumbing. Pockets have been fashioned into the cartridge walls to enhance colorimetric detection. The pocket depth is selected to minimize wall thickness while simultaneously preserving the mechanical integrity of the cartridge, especially in relation to the wider bores required for the pockets that contain accessory reagents. The wall angle, with respect to the four relatively square sides of the cartridge, can be adjusted to promote effective illumination and to attenuate harsh reflections of excitation light in particular.

Figure 9:
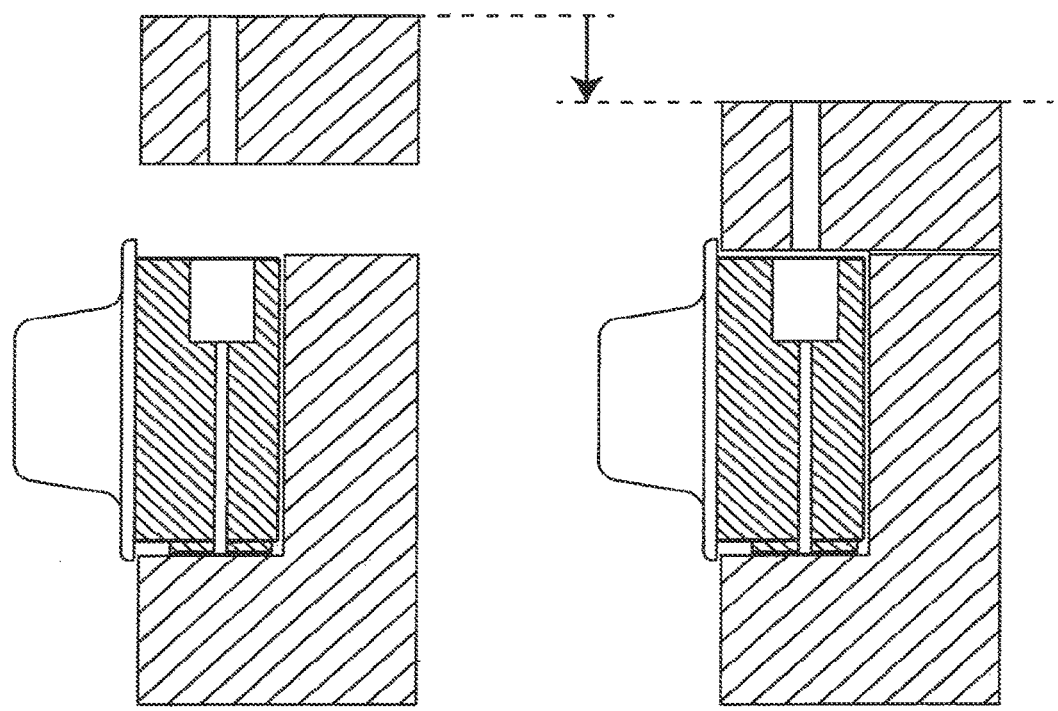
FIG. 9 shows a cartridge insertion into a base unit that makes use of a linear actuator.
Figure 10:
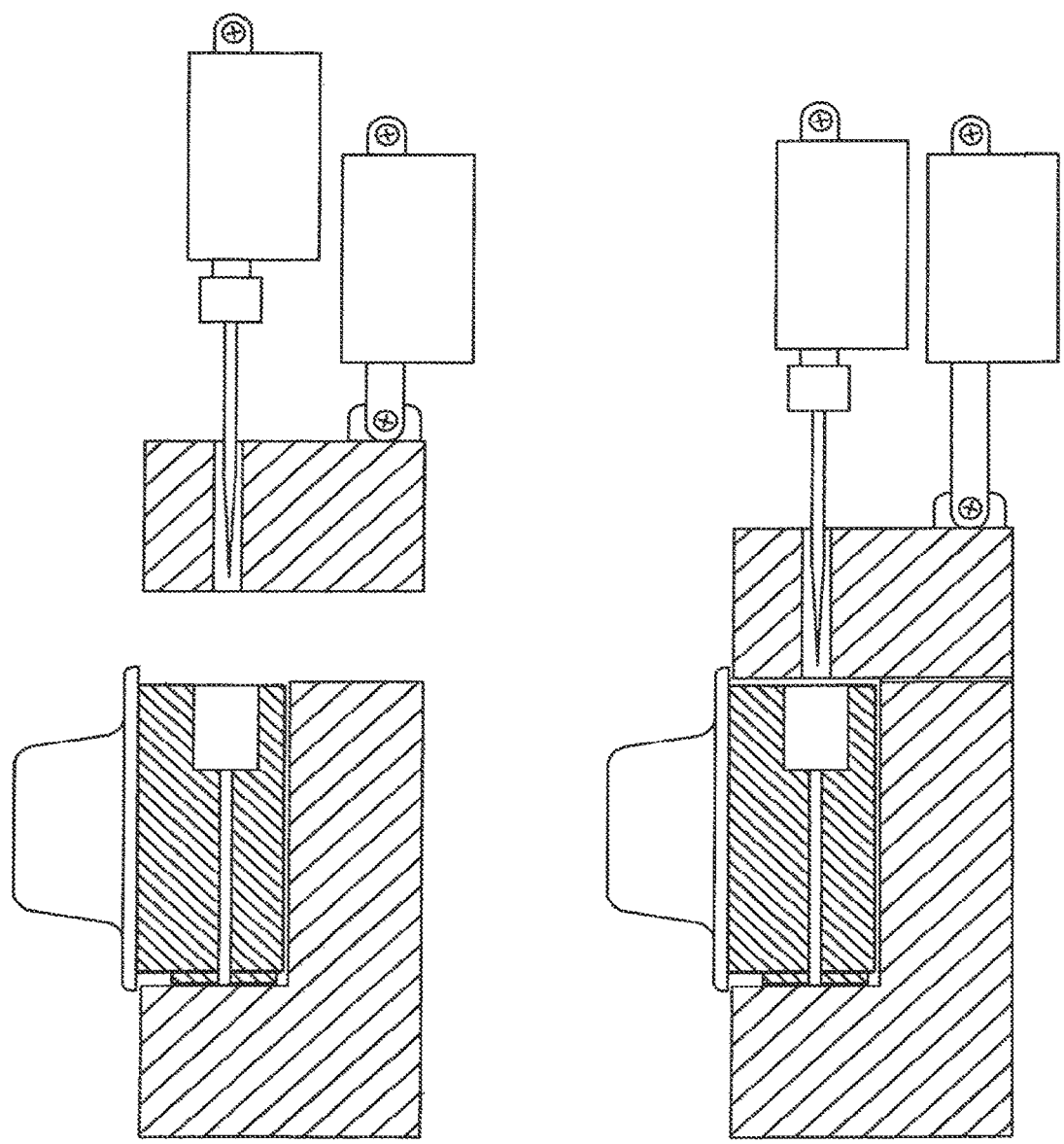
FIG. 10 shows the details of an embodiment of a sliding mechanism in relation to a sensor cartridge.
Figure 11:
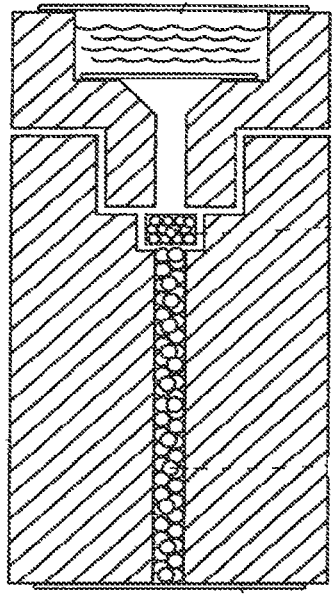
FIG. 11 shows an example of a breath gas analyzer column based on Tenax TA.
Figure 27:
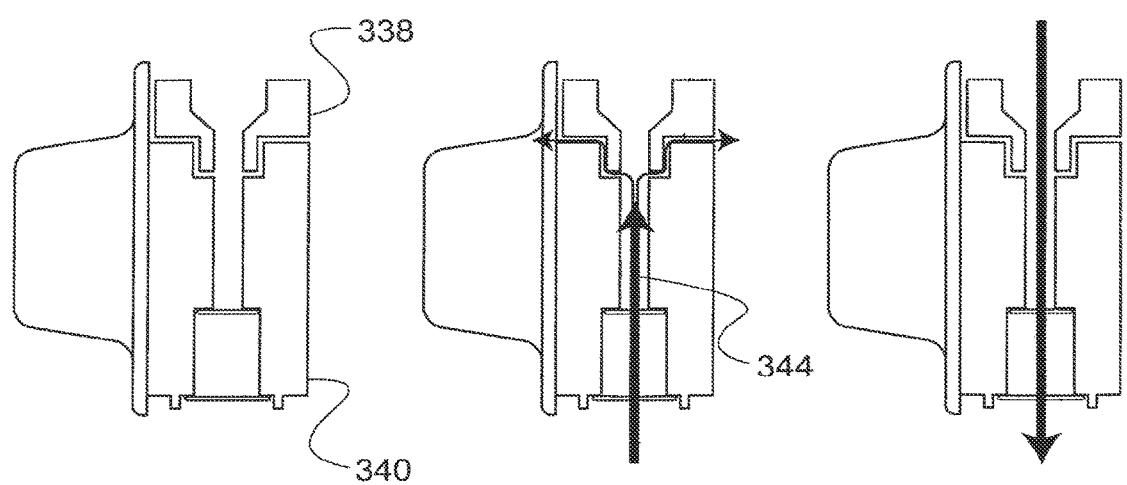
FIG. 27 shows a depiction of the flow path after the liquid seals have been broken and a liquid seal is formed.

One preferred example of how a cartridge interacts with a base unit is in the following manner. First, the user opens a door through the wall of the base device and places the cartridge into a cartridge receptacle. No significant force is required of the user to make the insertion, and insertion orientation is restricted by mechanical stops. Either of two (of the four) sides of the cartridge must be oriented toward the optical setup. A cartridge receptacle that receives the cartridge at an angle (whereby the top portion of the cartridge is inclined away from the user with respect to the bottom portion) increases user accessibility and comfort during cartridge insertion. Once the cartridge is loosely placed within the device, mechanical means are provided whereby the topside of the cartridge is compressed against a captive gasket in the base device. See FIG. 9 and FIG. 10. This compression forms a face seal between the gasket and the bottom of the cartridge, providing a leak-free fluidic connection capable of withstanding the driving pressure required to move breath samples and developer solution through the cartridge and its various compartments. Once the cartridge is in position, a breath sample is collected through various means, for example a breath collection bag or sidestream sampling. Once a sample of gas is ready for measurement, a pneumatic handler is actuated which withdraws breath gas from the gas collection vessel and pumps it first through the desiccant bed, next through the reactive column, and out through the cartridge. See FIG. 27. The cartridge is designed to be open to gas flow at both ends. The bottom side (desiccant side) is open through a woven mesh barrier, the top-side is open through the non air-tight sealing of the top piece (338) to the base (340). Thus, when gases are pushed through the bottom of the column, they can vent through the top although the developer containment barriers have not been broken. After the proper volume of breath sample has been pushed through the column at the selected rate of flow, the developer solvent containment means is ruptured. See FIG. 21. A sharp pin (236) is driven through the lid of the cartridge such that it breaks the top barrier (252) of the containment means first, then the bottom. Slower pin drive speeds and appropriate contained volumes of developer are preferred to prevent developer spillage during rupture. Also preferred is the ability of the containment means to withstand deformation during rupture when such deformations result in spilled developer solution. Once the developer is released, it fills the conical pocket (250). The conical pocket assists in creating a liquid seal (251), such that when fluid is pulled through the column (246) there is a continuous pull of developer into the column. The amount of developer pulled through the column can be controlled (open-loop) by adjusting the duration of the pulling pump's on cycle, or closed-loop means can be employed. An imaging system (see FIG. 4 and FIG. 5) is used to record colorimetric responses which result from analyte reaction with the reactive bed and developer solution. Developer solution can be largely contained in the desiccant bed. Optional top and bottom septa can be built into the cartridge when potential user exposure to especially deleterious solvents should be prevented.

FIG. 13 shows a preferred method for single-analyte cartridge construction. A single piece of molded clear plastic (120) such as acrylic forms the cartridge housing. A particle retention barrier (122), as previously described, is attached to the bottom of the flow channel but is comprised preferentially of thermal adhesive-backed (Fastel 15066, 3 mil thick) polyimide (Devinall, 2 mil thickness) with woven nylon center (198×198 mesh, 0.0031" opening, 49% open). Desiccant material (30-60 mesh anhydrous calcium chloride) fills a desiccant chamber (124). A particle retention barrier (126) similar to (122) is placed on the bottom to contain a desiccant. The reactive materials (100-140 mesh aminated and nitroprusside-attached particles in a 2:1 ratio) are placed in the flow column (128), and the top portion of the channel opens to facilitate low-tolerance filling. A porous material (130) such as glass wool, stainless steel mesh, or porous hydrophilic polyethylene plastic (preferentially) is placed over the reactive particles. In some embodiments, the reactive particles (128) and porous barrier (130) may need additional means to be compressed tightly against the particles. An o-ring, external toothed push-on ring, or deformable retainer ring may be suitable for this purpose, but porous plastic can make its own compression fit without the need of these means. A piercable liquid ampoule (133), comprised preferentially of a thermoplastic, heat-sealed can with pierceable barriers on top and bottom, is placed into a holding housing in a manner that does not occlude airflow. The top of the cartridge is sealed with a piercable foil (134) and a liquid barrier septum layer (136), such that liquid cannot leak through the lid after the cartridge has been used.

Figure 28:
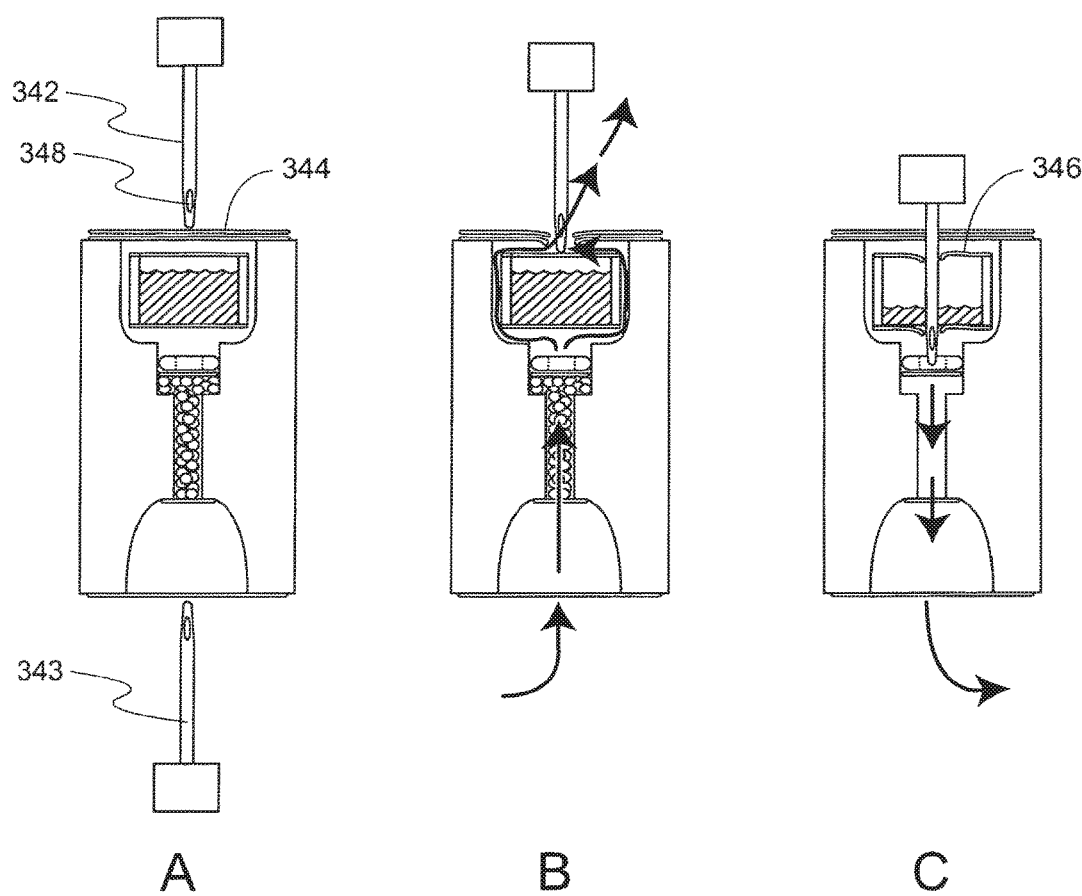
FIG. 28 shows an embodiment of a cartridge with a developer solution.
Figure 29:
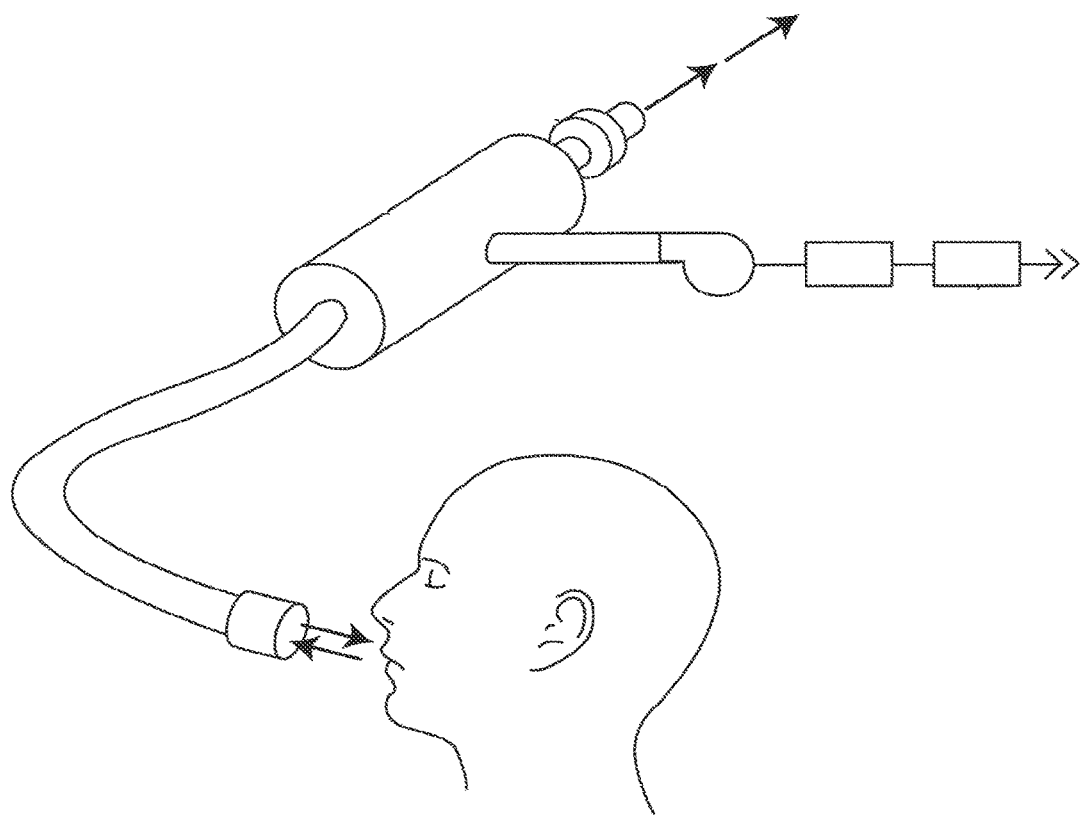
FIG. 29 shows an embodiment of a breath sampling loop based on multiple breath exhalations into a base unit.
Figure 30:
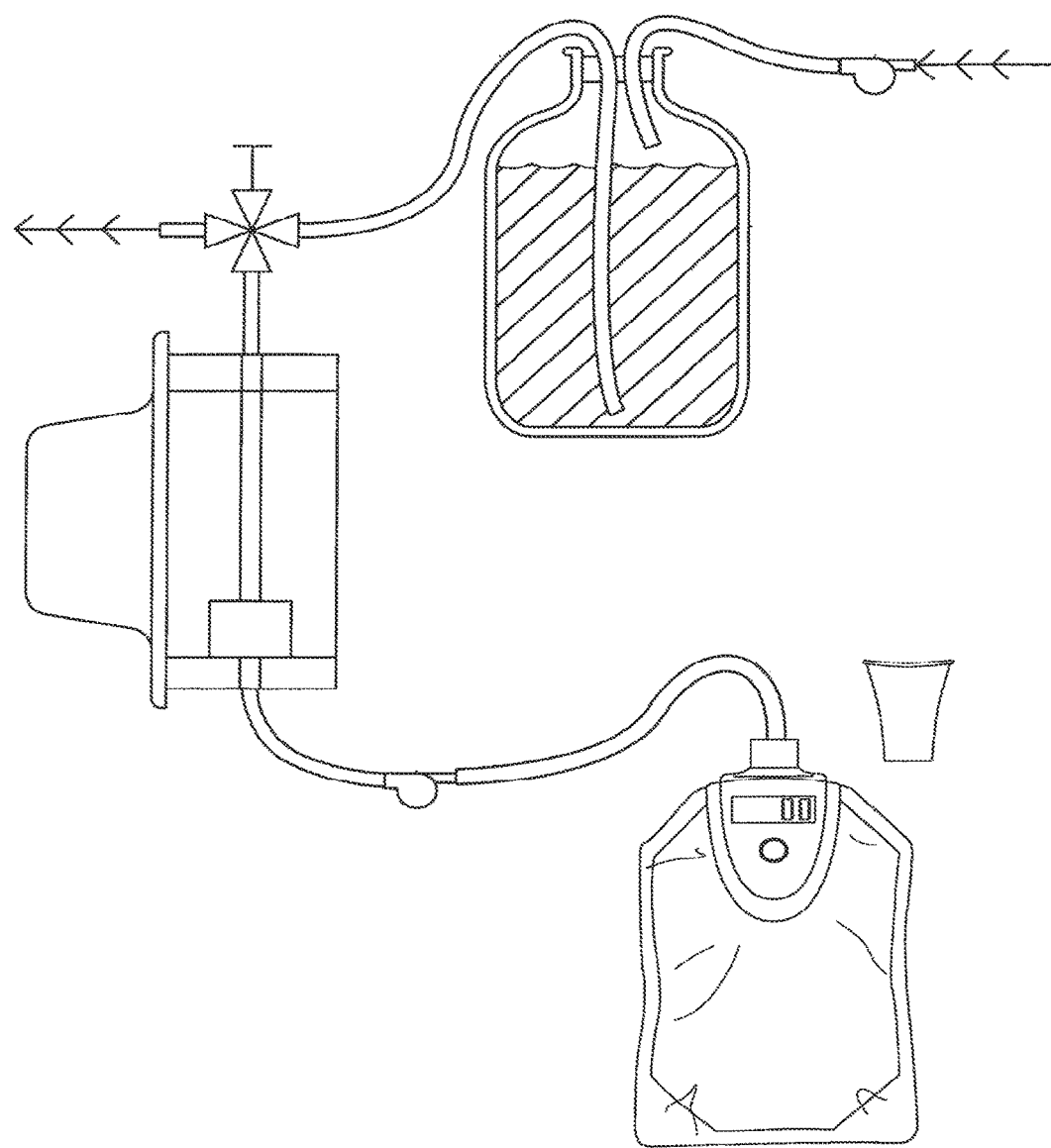
FIG. 30 shows an embodiment of a breath measurement system with the developer solution inside a replaceable container in the base unit instead of in disposable cartridges.

FIG. 28 shows a preferred method for using the cartridge discussed in FIG. 13. With the piercing needle (342) in the fully retracted position (A), the top barriers (344) have not been breached and airflow through the cartridge is not possible. With the needle in a first extended position (B), the top barriers are breached such that gas can flow from the bottom of the cartridge through the various porous barriers, reactive bed, around the liquid ampoule, and through the hole in the piercing needle (348). In a second extended position (C), liquid is released from the ampoule (346) and is pulled by suction force of a pump or by wicking downward through the reactive bed. A needle in the base unit (343) can be used to pierce a bottom barrier material to allow gas flow into the cartridge. This method allows the cartridge to be sealed for storage and shipping and to be automatically pierced upon usage without extra user steps. Also, the septum on top and extra barrier on bottom can be used to contain the liquid inside the cartridge after use. Note that the barrier to contain desiccant or other conditioning materials is not shown in this figure.

In accordance with one aspect of the invention, a method is provided for analyzing acetone in breath. The method comprises providing a cavity, locating within the cavity a primary amine disposed on a first surface, locating within the cavity a nitroprusside on a second surface distinct from the first surface, wherein the nitroprusside is coupled to the second surface using a coupling agent comprising an anion exchange resin in an acidic environment, wherein the acid environment comprises an acid having a vapor pressure of less than about 1 atm at 22 C in its 99% pure form, the primary amine on the first surface and the nitroprusside on the second surface comprising cavity contents having a reference optical property, causing the breath to move into the cavity so that it contacts the primary amine and the nitroprusside to cause or facilitate a change in an optical property of the cavity contents relative to the reference optical property, and analyzing the breath for the presence of the acetone using the change in the optical property.

Figure 31:
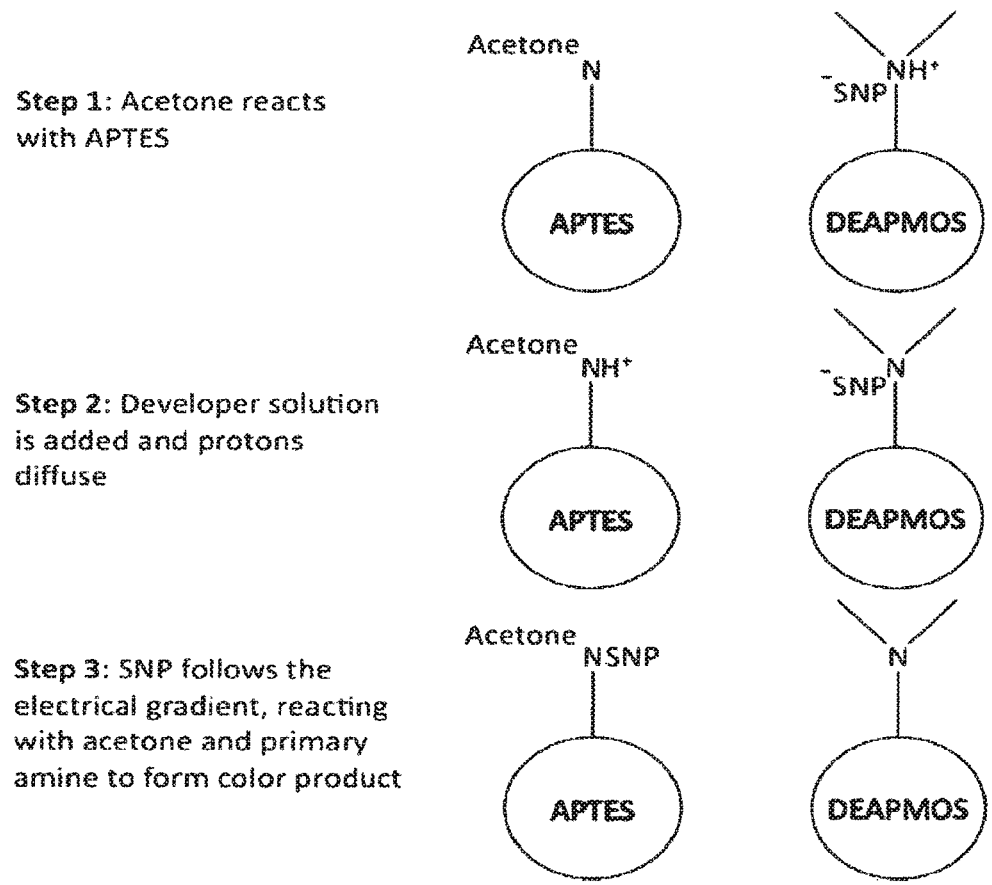
FIG. 31 shows a reaction scheme for analyzing acetone in breath.

A summary of a preferred implementation of this method is shown in FIG. 31. This method can be advantageously implemented using the breath analysis device shown in FIG. 1 and described herein above, or in the '862 application. The cavity according to this method preferably comprises an enclosed, and preferably elongated, volume or zone in which one or more reactants (most notably the primary amine) can be contained and wherein reaction of the acetone with the primary amine and/or other reactants (e.g., the nitroprusside) can take place. In presently preferred implementations of this method, the cavity comprises the principal cavity or chamber in the cartridge as shown in the drawing figures.

Moisture may have deleterious effects on the constituents and reactions involved in this method, as more fully described herein below, and thus the cartridge also preferably comprises a moisture control component to reduce or substantially eliminate moisture from the breath sample as it enters the cartridge, and before the breath sample is passed into the cavity.

As noted herein above, the method comprises locating within the cavity a primary amine disposed on a first surface. This aspect of the method preferably locates one or more primary amines in the cavity or reaction zone in a manner that facilitates contacting of the acetone with the primary amine or amines and reaction of the two. The primary amine may comprise any aliphatic primary amine. Aliphatic primary amines are capable of forming a Schiff base upon reaction with acetone, which forms a color product when coupled to nitroprusside. Primary amines that can be coupled to a surface are preferable. Examples of such primary amines include amino silanes, such as aminopropyltriethoxysilane. Although not wishing to be limited to a particular theory, the primary amine or amines are believed to react with the ketone body, preferably acetone, to form a Schiff base. The nitroprusside then reacts with the Schiff base to yield the optical property change.

In presently preferred embodiments and method implementations, the primary amine comprises an amino silane.

The first surface comprises a surface that will support and immobilize the primary amine or amines, so that they can be contacted by the acetone in the breath sample and favorably react with the acetone. The first surface preferably comprises a plurality of beads that, when in the cavity, comprise a packed bed.

In some embodiments, the reactive chemistry is coupled to the surface by using a coupling agent. "Coupling agents" are broadly defined as chemicals, molecules or substances that are capable of coupling (see definition for "react") a desired chemical functionality to a surface. Preferred coupling agents either have branched chemical functionalities or are capable of branching during coupling with the surface. "Branched chemical functionalities" or "branching" refers to having more than one chemically reactive moiety per binding site to the surface. Branching may be contained within a single coupling agent or may be achieved through the reaction of several coupling agents with each other. For example, tetraethyl orthosilicate may be mixed with aminopropyl trimethoxysilane for enhanced branching during the reaction.

There are numerous coupling agents known to those skilled in the art. In the class of silanes, there are literally thousands of functional chemistries attached to a silane. Silanes can be coupled to dozens of surfaces, with a preference for silica surfaces and metal oxides, and are capable of de novo surface formation. Examples of common functional silanes include aminopropyl trimethoxysilane, glydoxypropyl triethoxysilane, diethylaminopropyl trimethoxysilane and numerous others.

Coupling agents possessing a free amine are readily coupled to surfaces with epoxides, aldehydes and ketones, among other chemical moieties. Coupling agents with epoxides, aldehydes and ketones can also be used with surfaces containing a moderate to strong nucleophile, such as amines, thiols, hydroxyl groups and many others. Some coupling agents are attached to the surface through a free radical reaction, such as acrylates and methacrylates among others.

Some coupling agents do not directly react with the breath analyte. Rather, they are intermediate agents. An "intermediate agent" is a coupling agent whose chemical functionality is to react with yet another coupling agent. For example, diethylaminopropyl trimethoxysilane is an intermediate agent in the reaction with acetone. It does not directly react with acetone, but reacts with sodium nitroprusside, which in turn reacts with acetone. Another example of an intermediate agent would be the use of glycidoxypropyl triethoxysilane, whose epoxide functional group could be reacted with a host of other molecules to achieve a desired functionality. Numerous intermediate agents are known to those skilled in the art.

In presently preferred embodiments and methods, the beads may be comprised of silica, quartz, aluminum oxide, alumino-silicates, silicon, copper, tin oxide, talc, inorganic oxides, or combinations thereof. A preferred embodiment comprises silica. The optimal size of the silica gel varies with the flow rate and desired detection limits. In general, the smaller the silica gel particles, the larger the surface area for extraction of acetone. With smaller silica gel particles, a higher extraction efficiency is achieved, higher flow rates can be used and less reactive material is required. In some embodiments, a short, intense color change is desired. In some embodiments, silica gel size is between about 20 and about 270 mesh, between about 100 and about 200 mesh, between about 130 and about 140 mesh.

Preferred coupling agents for coupling the primary amine or amines with the bead surface comprise aminopropyltriethoxysilane (APTES) and diethylaminopropyltrimethoxysilane (DEAPMOS).

The deposition of primary amines onto a surface can be accomplished in a number of ways. Most any non-volatile primary amine can be readily deposited onto a variety of surfaces by placing the amine in contact with the surface and drying. Drying can be done under vacuum or at elevated temperatures. Mixing while drying helps to ensure even deposition.

Some amines such as amino silanes, can be covalently attached to the surface, which is useful in preventing elution of the amines during subsequent solvent based reactions. In practice, the inventors hereof have used Tris amine and/or aminopropyltriethoxysilane (APTES) coupled to silica gel with equal effectiveness. The latter covalently binds to the silica gel and is not washed off during solvent based reactions.

"Nitroprusside" is an anion with molecular formula [Fe(CN)5NO]2-. The use of the term herein also includes its various salts, such as calcium nitroprusside or sodium nitroprusside. Nitroprusside is also referred to in the literature by different names, e.g., nitroferricyanide.

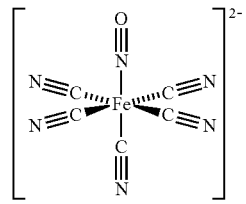

When used as a reactant or reagent, it is typically in the form of a salt, a common example of which is sodium nitroprusside ("SNP"). The nitroprusside according to presently preferred embodiments and method implementations comprises, and more preferably consists of or consists essentially of, sodium nitroprusside, although it is possible to use other salts or constituents that comprise the nitroprusside ion.

In accordance with this aspect of the invention, the second surface comprises one or more surfaces that support the nitroprusside. It preferably comprises a plurality of beads, which may but need not have the same composition or structure as the first surface supporting the primary amine. In presently preferred embodiments and methods, the second surface comprises a plurality of beads comprising silica, quartz, aluminum oxide, alumino-silicates, silicon, copper, tin oxide, talc, inorganic oxides, or combinations thereof.

The nitroprusside is coupled to the second surface using a coupling agent, preferably comprising an anion exchange resin or a tertiary amine. The coupling agent comprises anionic exchange resins per se, as well as polymeric materials that have anionic exchange properties or function a priori. Diethylaminopropyltrimethoxysilane is a presently preferred coupling agent.

In this method, the coupling the nitroprusside to the second surface is carried out in an acidic environment wherein the acid environment comprises an acid having a vapor pressure of less than about 1 atm at 22 C in its 99% pure form.

An acid other than a hydrogen halide is preferred. Hydrogen halides include the group of hydrogen chloride, hydrogen iodide, hydrogen bromide, and hydrogen fluoride. Hydrogen halides are gases in their pure form. Hydrogen halides mix with water to form acids. Hydrochloric acid is a mixture of hydrogen chloride gas and water. Pure hydrogen chloride has a vapor pressure of 43 atm at 22 C and a boiling point of −85 C. Hence, hydrogen chloride is an extremely volatile gas that can be somewhat stabilized in the presence of an excess of water. Since water is inhibitory to the reaction with acetone and must be removed, the remaining hydrogen chloride is volatile. It diffuses freely over time to the primary amines, lowering the reactivity of the primary amines. Further, without the hydrogen chloride to quench the tertiary amine, the tertiary amine is able to attack and degrade the nitroprusside. Salts that contain halide anions should also be avoided to prevent loss of protons through the formation of gaseous hydrogen halides.

Preferred acids include acids with a pKa less than about 4 and a vapor pressure less than about 1 atm at 22 C in its 99% pure form. Preferred examples include sulfuric acid, oxalic acid, nitric acid, phosphoric acid, perchloric acid, but there are many others known to those skilled in the art. A preferred acid for this purpose is or comprises sulfuric acid. Acids with a pKa less than 4 are capable of lowering the pH of the tertiary amine below 4. With a vapor pressure of less than 1 atm at 22 C in their 99% pure form, they are relatively stable over time. This reduces the migration of protons from the tertiary amine to the primary amine and better preserves the nitroprusside and reactivity of the primary amine.

The primary amine on the first surface and the nitroprusside on the second surface comprise the principal contents of the cavity in presently preferred embodiments and methods. These contents collectively have certain optical properties, such as color, color variation, transparency or translucence, optical absorptivity, and the like. When viewed collectively, e.g., when viewed macroscopically with the unaided human eye or with a standard digital camera, have a general color. In the initial state of the analysis, with the reactants (the primary amine and nitroprusside) intact, the cavity contents have an initial or reference optical property or set of properties. As reactions occur as described herein, the optical property or properties are expected to change as a result of those reactions. These changes in the optical property or properties can then be sensed and measured, and thus can be used to assess the extent of the reaction, and the nature and amount of initial reactants, most notably the presence and amount of acetone in the breath sample.

The reference optical property preferably comprises a reference color, and the change in optical property preferably comprises a change in color with respect to the reference color.

The cavity has a linear dimension, and the reference optical property comprises a reference distance of the reference color along the linear dimension. The change in optical property preferably comprises a measured distance along the linear dimension of the change in color with respect to the reference color.

As the breath sample is moved into the cavity, it contacts the primary amine and the nitroprusside to cause or facilitate a change in an optical property of the cavity contents relative to the reference optical property.

A number of means may be used to react the primary amine or amines with the ketone body, and this is not necessarily limiting. The contacting and reaction may take place, for example, in solution.

Although not wishing to be bound by any particular theory or mechanism of reaction, it is believed that acetone optimally forms a Schiff base with a primary amine under slightly acidic conditions, e.g., at about a pH of 5. In practice, however, the inventors hereof have not observed a significant difference in extraction efficiency or kinetics of reaction with primary amines (Tris, APTES, etc.) on silica gel from a pH of 1.0 to 11.0. The rate limiting step is believed to be the reaction of the Schiff base with nitroprusside. Binding APTES to silica gel with no acid added has a pH of roughly 10.

The presence of water in the sample or in the substrate where the primary amines are found reduces the binding efficiency, presumably through the reversal of Schiff base formation. In practice, the inventors hereof have discovered that humid samples cause the acetone to bind over a longer distance and slow the color development. Extraction or reduction of the water from humid samples to an acceptable low level is a requirement to maximize acetone extraction efficiency and kinetics of color formation.

Optionally but preferably, the method comprises using a developer solution to facilitate the change in the optical property. In the preferred embodiments and method implementations, the developer solution comprises 0.5% diethanolamine in 25% dimethylsufoxide, and 75% methanol. The use of the developer solution in this embodiment and in others in this application serves primarily two purposes: 1) to deliver or enhance delivery of nitroprusside (i.e., by diffusion or convection) and/or 2) to alter the pH.

As a general principle, the developer solution preferably should be anhydrous and should contain anhydrous components. The presence of water slows color formation, presumably due to the reversal of Schiff base formation. It should be noted that reagents that form water (e.g., NaOH) during the reaction may be unsuited for certain applications.

As mentioned previously, SNP can be stabilized in solution through the use of an acidic medium. Rather than being dried onto a surface, the SNP can be stored in the developer solution itself. In practice, low pH solutions (e.g., 1.0) are not ideal for developing the acetone reaction on columns. Presumably, the large number of protons quickly saturate the amines on the surface, creating a large positive charge which extracts the negatively charged nitroprusside anion from solution before it reaches the reaction site. The nitroprusside is visibly extracted on the surface in these cases. The low concentration of downstream SNP reduces both sensitivity and reaction kinetics. However, this obstacle can be overcome by: 1) using a larger amount of developer solution, 2) using a smaller amount of aminated surface, 3) adding the developer solution from the same side that the sample is added, or 4) using a less acidic solution. A pH of 4 has a much less visible effect, while a pH of 7 does not have any observable effect.

Basic developer solutions degrade nitroprusside in solution, although high concentrations of nitroprusside can be used to quench the base. Generally basic developer solutions are more suitable for reactions where nitroprusside is deposited in a more stable acidic state elsewhere, whether in solution or coupled to a surface.

When coupled to primary amines at a low pH, the pH must be raised above a threshold level before the Schiff base will detectably react with nitroprusside. The selection of the base to remove the proton is important. Only bases with a similar or higher pKa for their conjugate acid will have the strength to rapidly deprotonate the amine. In general, the stronger the base, the faster and more complete the deprotonation. Further, concentrations of base in the developer solution are important for both kinetics and the ability to remove sufficient protons to raise the pH.

In systems where the developer solution is passed across a relatively large amount of protonated amines or surfaces, a pH gradient can form. Where the developer solution first contacts the amines, a high pH will be created, turning unreacted nitroprusside a yellow color. However, downstream as the base in the developer solution is used up, the pH remains relatively low and the nitroprusside appears a reddish brown color, which can be confused for a positive acetone signal.

Sufficient developer solution must be passed across the surface in order to remove the pH gradient and form a constant pH. In practice, the inventors of the present invention have achieved this by either pushing the developer solution through or by placing sufficient wicking material on the other side of the aminated surface to pull a large volume of developer solution through.

When the primary amines are not heavily protonated (i.e., the pH is close to the pKa of the conjugate acid), the strength of the base can be lower. A relatively weak base compared to the primary amine can be used in this case. This prevents a positive charge from accumulating in the developer solution which can carry nitroprusside downstream.

The method according to this aspect of the invention further comprises analyzing the breath for the presence of the acetone using the change in the optical property. This is preferably achieved by observing and measuring the optical property change. In the preferred embodiments and methods, this is carried out using the digital camera and other components of the optical subsystem, as described herein above and in the '862 application.

Figure 36:
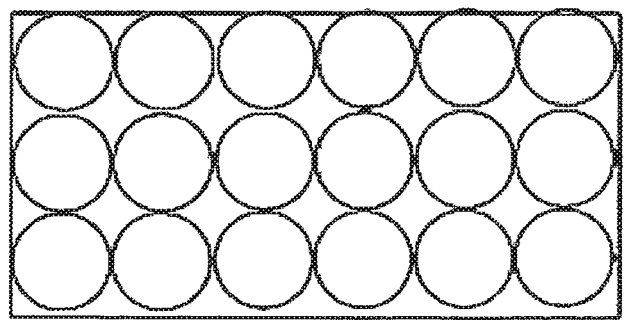
FIG. 36 shows optical characteristics of the reaction zone.
Figure 36:
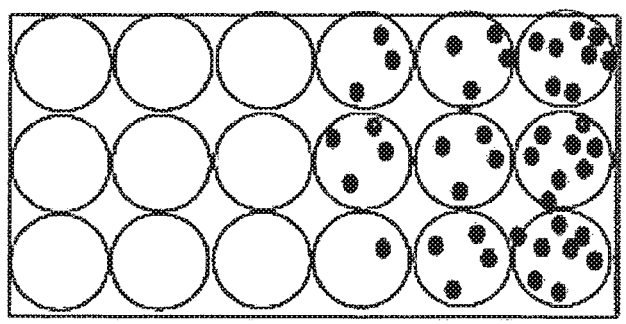
Figure 36:
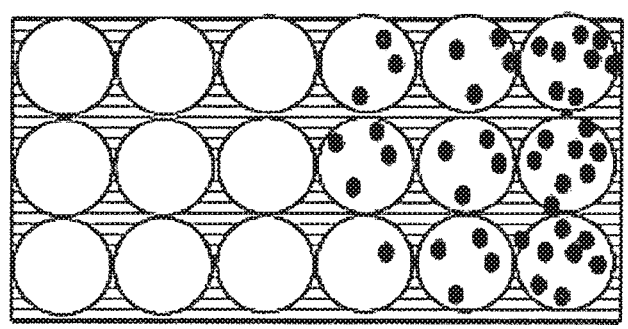
Figure 36:
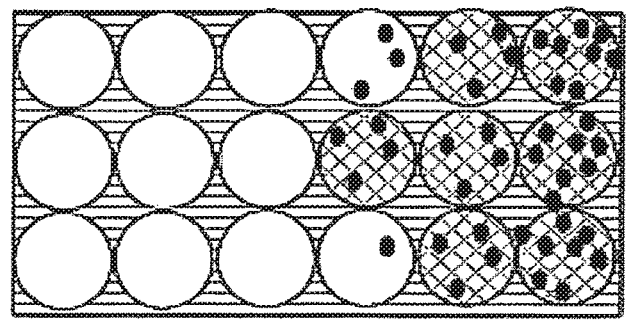

FIG. 36 shows the sequence of changes in optical characteristics of the reaction zone during the optical detection of acetone in certain embodiments. Panel A shows reactants disposed in a reaction zone prior to delivering the breath sample to the interactant region. Dry reagents exhibit an optical characteristic at a first reference level. As shown in Panel B, during delivery of the breath sample to the reaction zone, the analyte adheres to the reactant but does not exhibit an appreciable or selective change in the optical characteristic of the reaction zone with respect to the first reference level. Panel C shows the generation of an optical characteristic at a second reference level caused by addition of a developer. This state is intended to illustrate the optical change in the reaction zone due to administration of the liquid developer. In some cases, the second reference level exhibits a change in spectral content from the first reference level, but in other cases this change may be the result of a refractive index change without significant spectral shift. In some cases, this state may be so brief as to be unobservable but in other cases there will be a significant dwell time in this state. Panel D illustrates, for example, the development of color in the reaction zone, comprising an optical characteristic at a third level, which is a change with regards to the second reference level. In other embodiments, the change caused by, for example, Panel D may be compared to the first reference level of Panel A.

In accordance with another aspect of the invention, a method is provided for sensing acetone in breath using a breath analysis device. This method, among other things, addresses the instability of the nitroprusside in an aqueous alkaline environment. As noted herein above, a traditional approach to the use of a nitroprusside and a primary amine to detect acetone has been to mix or intermingle the nitroprusside and the primary amine prior to introduction of the acetone. This created technical issues because the alkalinity of the primary amine degraded the nitroprusside. Even when acids such as hydrochloric acid were used to reduce the alkalinity and thus stabilize the nitroprusside, degradation still took place, albeit at a slower pace.

The method according to this aspect comprises disposing a reactant in a reaction zone within the breath analysis device, wherein the reactant comprises a primary amine disposed on a surface, and wherein the reaction zone has an optical characteristic that is at a reference level.

In this method, however, the nitroprusside is provided in the form of a liquid solution within the breath analysis device, but pre-stored separately from the reactant. The method further comprises using the breath analysis device to cause the breath to contact the reactant in the reaction zone so that the acetone in the breath reacts with the primary amine to form a reaction product and, after the reaction product has been formed, using the breath analysis device to cause the nitroprusside solution to contact and react with the reaction product and to facilitate a change in the optical characteristic of the reaction zone relative to the reference level. The method also comprises using the breath analysis device to detect the change in the optical characteristic to sense the acetone in the breath.

By separately pre-storing the nitroprusside, degradation is avoided. Moreover, by providing it as a liquid, it can be more easily dispensed into the primary amine, and it can serve as, or double as, a solvent or developer solution.

In presently preferred implementations of this method and embodiments of related breath analysis devices, the primary amine is disposed on a plurality of silica gel beads. Small bead sizes, such as a size distribution between 100 and 270 mesh, are preferred so that sensitivity and bed efficiency are heightened.

In preferred implementations of the method, the primary amine component is maintained in an alkaline environment, in the absence of any volatile acids. The primary amine bed may be quenched with a non-volatile acid, for example, but preferably, such as sulfuric acid.

The pre-stored liquid nitroprusside solution preferably is in a non-alkaline environment, and consist essentially of a non-alkaline solution. Preferably there are not components in the nitroprusside solution that have a base dissociation constant less than 6. The pre-stored nitroprusside solution also preferably is quenched with a non-volatile acid, such as sulfuric acid. This quenching preferably is undertaken so that the liquid nitroprusside solution has a pH of less than 8, and more preferably below 7. To further avoid degradation, the liquid nitroprusside solution also preferably is stored in the absence of ambient light. This may be achieved by providing the liquid in an ampoule or other container that has an opaque outer coating so that light is excluded during pre-storage.

In accordance with still another aspect of the invention, a method is provided for sensing acetone in breath using a breath analysis device. In this method, degradation of the nitroprusside is avoided by pre-storing a nitroprusside in a non-alkaline environment.

The method comprises disposing a reactant in a reaction zone within the breath analysis device, wherein the reactant comprises a primary amine disposed on a surface, and wherein the reaction zone has an optical characteristic that is at a reference level. As noted, a nitroprusside is pre-stored in the breath analysis device in a non-alkaline environment. The method further comprises using the breath analysis device to cause the breath to contact the reactant in the reaction zone so that the acetone in the breath reacts with the primary amine to form a reaction product. After the reaction product has been formed, the method comprises using the breath analysis device to cause the nitroprusside to contact and react with the reaction product and to facilitate a change in the optical characteristic of the reaction zone relative to the reference level, and using the breath analysis device to detect the change in the optical characteristic and to sense the acetone in the breath.

The non-alkaline environment for the pre-stored nitroprusside according to this aspect of the invention, which preferably does not include any components or substances with a base dissociation constant less than 6, can be achieved by quenching the primary amine on the surface with a non-volatile acid, e.g., such as sulfuric acid, so that the primary amine on the surface has a pH that is less than 8, and more preferably less than 7.

Given the different characteristics of the primary amine and the nitroprusside, the method preferably comprises pre-storing these two components separately, preferably using a gas-tight barrier or other means of isolation.

The nitroprusside component may be in the form of a liquid, but it also may be in solid form. In a preferred implementation of the method, both the primary amine and the nitroprusside are disposed on silica gel beads having a mesh size of about between 100 and 270. The beads are intermingled. A liquid developer solution is dispensed on the intermingled beads, which enables the reactions that give rise to the change in optical characteristic.

EXAMPLE 1

APTES beads were made by adding 0.5 grams ("g") of 130 to 140 mesh silica gel to 200 microliters ("uL") of APTES in 800 uL of propanol and drying at 80° C. Following drying, the APTES beads were cured at 110° C. for one hour ("hr"). This was done to create the "first" surface.

DEAPMOS beads were made by adding 0.25 g of 130 to 140 mesh silica gel to 100 uL of DEAPMOS and 400 uL of propanol and drying as described above. Following drying, 0.25 g of the beads were added to 0.75 mL of 1 normal ("N") sulfuric acid (H2SO4) and 0.25 milliliters ("mL") of diH2O and incubated for 10 minutes ("min.") while rocking. 0.1 g of sodium nitroprusside ("SNP") and 0.04 g of magnesium sulfate (MgSO4) were dissolved in the mixture, and then the beads were vacuum filtered and dried at 110° C. for 20 min. 0.25 g of the DEAPMOS/SNP beads were then mixed with 0.5 g of APTES beads and packaged into separate aliqouts. This was done to create the "second" surface.

The beads were packed into a ⅛ inch ("in.") inside diameter Tygon tubing that was 0.3 in. long. 0.5 parts per million ("ppm") of acetone in dry nitrogen gas (N2) was passed across the beads at 200 mL/min. for 3 min. Then 90 uL of developer solution (0.5% diethanolamine in 25% dimethylsulfoxide, 75% methanol) was added to the beads and the mixture was allowed to incubate for 3 min. prior to imaging. When viewed at 3 min., a short, but easily visible, color bar was observed.

The use of an acidic environment to create the "second" surface, and particularly the use of an acid with a vapor pressure less than about 1 atm at 22 C in its 99% pure form, provides significantly improved stability and results over prior known approaches. If this method had been implemented using HCl instead of sulfuric acid, the stability of sodium nitroprusside would have been relatively low. The pH of the primary amines would have also changed over time, reducing the reactivity of the primary amines. Although HCl (i.e., the acid reportedly used by Abbott) temporarily stabilizes the SNP, the HCl is extremely volatile. The tertiary amines eventually regain their alkalinity to the degree that HCl is lost. This results in the rapid degradation of SNP. Based on tests conducted by the inventors hereof, the method using HCl (0.5 g DEAPMOS beads manufactured with 1 mL 1 N HCl) fails in less than 12 hrs at 102° C. This is in contrast to the method using H2SO4 (0.5 g DEAPMOS beads manufactured with 1 mL 1 N H2SO4), which lasts more than 4 times as long at 102° C.

Restricting the volatility as set forth herein above, e.g., using a less volatile acid than HCl, significantly improved results. In this specific example, using H2SO4, the method quadrupled the stability to 48 hrs at 102° C. over the HCl configuration reportedly used by Abbott, which is equivalent to 6 to 12 months at room temperature.

Because of the proton coupling to the tertiary amine, a strong positive charge is present on the tertiary amine beads, making dissociation of the SNP very slow. Due to reversibility of the Schiff base formation, however, water should not be used. DMSO is added to help stabilize the Schiff base formation. Methanol does not have sufficient polarity to solvate the nitroprusside in the presence of the positively-charged tertiary amine. A weak base, such as diethanolamine, is preferred to help the protons diffuse, creating a charge gradient for the nitroprusside to follow. Also, once the nitroprusside is in solution, it still must diffuse to the primary amines before the desired reaction will take place. The kinetics of reaction with a tertiary amine adjusted to an appropriate pH level can require up to 10 min. for a complete reaction at 0.5 ppm of acetone.

The sensitivity achieved with this preferred method implementation also was superior. Presumably this is due to a higher concentration of nitroprusside than that used in the method disclosed by Abbott. While subtle differences may exist, the overall results were pronounced. In Example 1, a breath sample containing 0.5 ppm of acetone yielded a change visible as a very short dark line following a lengthy development time.

In summary, according to the Abbott patents, Abbott coupled SNP to a tertiary amine synthesized from ethylamine and an epoxysilane. They adjusted the pH of the tertiary amine component to 4.5 using HCl.

Using the method as set forth in Example 1, the present inventors quadrupled the stability (e.g., length of time that it is stable) by using H2SO4 instead of HCl to pH adjust the tertiary amine. By using a higher concentration of SNP the sensitivity and kinetics were enhanced. The SNP was also coupled to the beads with a different chemistry, i.e., diethylaminopropyl trimethoxysilane, which provides the added benefit of simplifying manufacturing.

The Schiff base is capable of attacking the nitrosyl group of the nitroprusside under the right conditions. And in doing so, it forms a colored product that is visible to the eye.

Nitroprusside reportedly reacts with Schiff bases under alkaline conditions. The literature generally reports that the optimum pH is equal to the pKa of the conjugate acid, where 50% of the amino groups forming the Schiff bases are protonated. For an aminopropyl silane, the optimum pH is just over 10. In preferred embodiments and methods, the pH of the primary amines is adjusted between about 9 and about 11, between about 10 and about 10.5. Lower pH values are believed to completely protonate the Schiff base, precluding it from reacting with nitroprusside. Higher pH's tend to hasten the degradation of the colored product and have no positive charge to attract the nitroprusside with. In practice, we have observed the fastest kinetics for nitroprusside reaction with Schiff bases formed from aminopropyl silane near a pH of 10. The nitroprusside does not visibly react under highly acidic conditions.

Since the kinetics of Schiff base formation are relatively fast, the reaction is rate limited primarily by the nitroprusside reaction with the Schiff base. Hence, the kinetics are governed principally by nitroprusside concentration, pH and stability of Schiff base formation (e.g., the absence of water).

The stability of nitroprusside is one of the determinants of the stability of acetone tests using nitroprusside. Nucleophiles react with nitroprusside. Even weak nucleophiles such as water are capable of degrading nitroprusside.

In SNP/acetone reactions, low pH's are not used on the primary amines or in the developer solution because they prevent nitroprusside from reacting with the Schiff base. Nitroprusside is greatly stabilized by acid. This is believed to be because it quenches any nucleophiles, thus preventing degradation. When nitroprusside is dried or in solution with acid, it appears to be indefinitely stable in pH of 1, even in the presence of nucleophiles. In practice, some stability is observed at a pH of 7, but order of magnitude increases are observed at lower pH's.

Nitroprusside is generally considered to be unstable in solution. However, the inventors of the present invention have discovered that, in low pH, nitroprusside is very stable in solution. But even at high pH, nitroprusside can be stabilized when present at high concentrations. This is believed to be because the nucleophiles present in solution are at a lower concentration than the nitroprusside and are quenched through reaction with nitroprusside. At sufficiently large concentrations, this has a negligible impact on the amount of active nitroprusside left in solution. In practice, the present inventors have put sufficient nitroprusside in solution to quench even 0.1 M NaOH. Nitroprusside appears indefinitely stable in solution with no nucleophiles present when protected from light. Examples would be nitroprusside in diH2O or in a methanol/DMSO solution.

Nitroprusside is generally considered to be unstable in the presence of primary amines. However, the present inventors have discovered that when primary amines are quenched with sufficient acid to lower the pH, nitroprusside can become indefinitely stable in their presence.

When protected from light and the ambient, nitroprusside is stable for long periods of time when dried onto surfaces with neutral pH and without nucleophiles. Examples would be silica gel or, less nucleophilic still, teflon or polystyrene, or various other materials known to those skilled in the art.

The base serves to enhance solubility of the nitroprusside. Until the positive charge on the surface is removed, very little nitroprusside is soluble, even in a mixture of 25% DMSO in MeOH over a period of 10 minutes. Also, the base enables color formation. Until the protons are removed from the surface, the nitroprusside remains in a completely protected form with no visible reaction. Where no pH change is necessary and the nitroprusside, e.g., SNP, is not coupled to a positively charged surface, no base is necessary.

The DMSO has an unexpected benefit. The Abbott patents mention that DMSO was added to "stabilize" color formation. In the single bead method described herein, a solution with APTES in methanol without DMSO appears to wash acetone and color products downstream. In contrast, when DMSO is added to the mix, the acetone/color product is more stable in the position it starts in.

Performing the reaction in the single bead method described herein without methanol (i.e., 62.5% DMSO, 37.5% APTES) yields no visible reaction. Although some of the nitroprusside was clearly in solution, methanol may be required to assist with dissociation such that nitroprusside becomes available for reaction. Also, substitution of propanol for methanol results in a uniform darkening of the reagent with or without the presence of acetone.

Holding DMSO constant at 25% and varying APTES concentration in methanol from 50%, 37.5%, 18.75%, and 9% showed that forward kinetics were roughly equal for 18.75% and higher concentration, but began to slow once APTES dropped to 9%. Destructive kinetics (i.e., loss of color formation) and violent bubble production inhibiting a clear and consistent view of the beads were substantially higher at 50% APTES. For rapid kinetics and minimum destructive/bubble kinetics, an APTES concentration of between 15 and 37% is preferred. However, lower concentrations, i.e., 10%, may be more suitable for smooth, consistent results on longer columns or with larger amounts of developer solution passing across the beads.

In accordance with another aspect of the invention, a method is provided for analyzing acetone in breath, wherein the method comprises providing a cavity, and locating within the cavity a primary amine disposed on a first surface. The primary amine on the first surface comprises cavity contents having a reference optical property. The method also comprises providing a nitroprusside in a nitroprusside solution initially separated from the primary amine on the first surface, wherein conditions of the nitroprusside solution when separated from the primary amine on the first surface are selected to stabilize the nitroprusside relative to the reactivity of the nitroprusside in the cavity with the primary amine. The method further comprises causing the breath to move into the cavity so that it contacts the primary amine to create a primary amine reaction product, and causing the nitroprusside solution to enter the cavity and the nitroprusside to react with at least one of the acetone and the primary amine reaction product, to cause or facilitate a change in an optical property of the cavity contents relative to the reference optical property, and analyzing the breath for the presence of the acetone using the change in the optical property.

Figure 32:
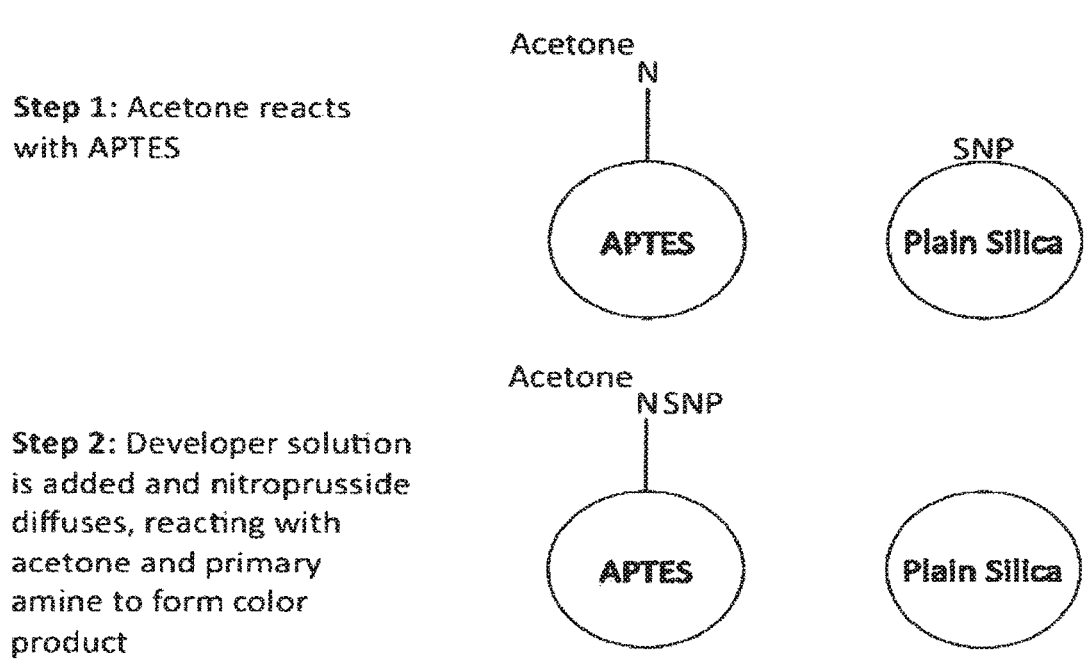
FIG. 32 shows a reaction scheme for analyzing acetone in breath.

A summary of the presently preferred implementation of this method is provided in FIG. 32. A preferred but merely illustrative method implementation of this aspect of the invention is provided by the following example.

EXAMPLE 2

APTES beads were made by adding 0.5 g 130 to 140 mesh silica gel to 200 uL APTES in 800 uL Propanol and drying at 80 C. Following drying, the APTES beads were cured at 110° C. for 1 hr. 0.5 g of APTES beads were added to 0.4 mL 1 N H2SO4 and 0.6 mL propanol and dried at 110° C. for 30 min.

Plain silica SNP beads were made by adding 0.3 g 130 to 140 mesh silica to 500 uL diH2O with 0.075 g SNP and 0.03 g MgSO4. Beads were dried at 110° C. for about 45 min. Plain silica SNP beads were mixed with APTES beads in a 1:2 ration and divided into aliquots Beads were packed into a ⅛" inside diameter column that was 0.3" long. 0.5 ppm acetone in dry N2 was passed across the beads at 200 mL/min for 3 min. Then 90 uL of developer solution (25% dimethylsulfoxide, 75% methanol) was added to the beads and allowed to incubate for 3 min prior to imaging. A short, but easily visible, color bar was present after only 30 seconds.

A neutral or "plain" surface does not have nucleophiles present on it, such as tertiary amines, and do not generally require the addition of extra acid. SNP is dried onto the surface and the surface is mixed with a second aminated surface, such as APTES beads.

The present inventors have used both silica and polystyrene as surfaces, but the potential embodiments are numerous. The polystyrene is inert whereas the silica does have hydroxyl groups that have some nucleophile potential.

The stability of SNP on either surface is believed to exceed that of the Abbott method. When acid is used, there is a problem with proton diffusion to the primary amines, changing their performance in a given developer solution over time. When no acid is used, the nitroprusside is stable on silica gel for more than 96 hours at 102° C. That is more than 8 times the stability seen in the reported Abbott method.

The neutral or plain surface has no net charge, so nitroprusside can be solvated with methanol on its own. However, DMSO helps the components go into solution very quickly and stabilizes the Schiff base. Because of diffusion, the kinetics are not much better than the Abbott method.

The neutral surface method as described herein does not develop a pH or charge gradient because protons are not used to stabilize or retain the SNP on the surface. However, as the SNP is solvated, it can form a slight gradient as it is washed away from the surface. Provided sufficient developer solution is used, this gradient appears minor for both the methanol and DMSO/methanol developer solutions.

In accordance with another aspect of the invention, a method is provided for analyzing acetone in breath, wherein the method comprises providing a cavity, and locating within the cavity a primary amine disposed on a first surface. The primary amine on the first surface comprises cavity contents having a reference optical property. The method also comprises providing a nitroprusside in a nitroprusside solution initially separated from the primary amine on the first surface, wherein conditions of the nitroprusside solution when separated from the primary amine on the first surface are selected to stabilize the nitroprusside relative to the reactivity of the nitroprusside in the cavity with the primary amine. The method further comprises causing the breath to move into the cavity so that it contacts the primary amine to create a primary amine reaction product, and causing the nitroprusside solution to enter the cavity and the nitroprusside to react with at least one of the acetone and the primary amine reaction product, to cause or facilitate a change in an optical property of the cavity contents relative to the reference optical property, and analyzing the breath for the presence of the acetone using the change in the optical property.

Figure 33:
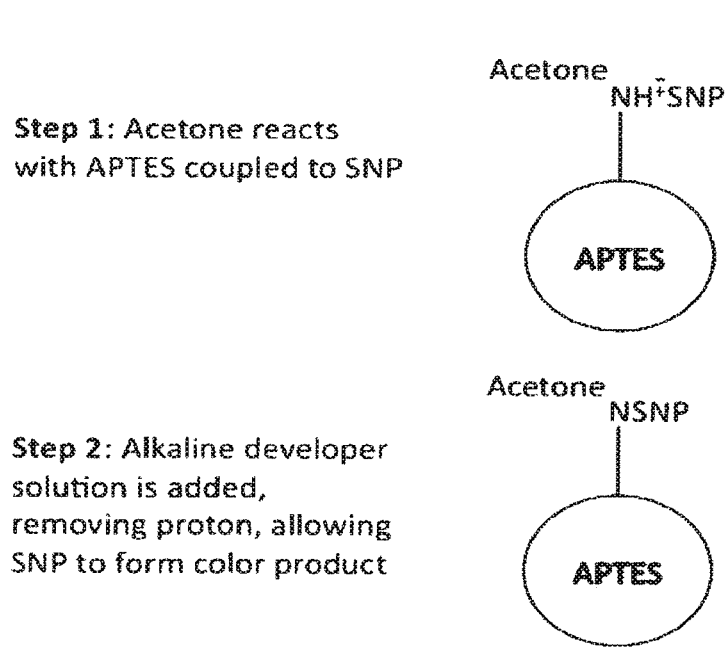
FIG. 33 shows a reaction scheme for analyzing acetone in breath.

A preferred implementation of this method is provided in FIG. 33.

An anhydrous nitroprusside solution can be made by dissolving between about 0.5 and 10%, between about 2 and 8%, between about 4 and 7% sodium nitroprusside in an anhydrous, organic solvent. In some embodiments, the organic solvent is an alcohol. In a preferred embodiment, the organic solvent comprises methanol. In an even more preferred embodiment, dimethylsulfoxide is added as a stabilizer, between about 1 and 50%, between about 10 and 40%, between about 20 and 30%.

The following example provides an illustration of this aspect of the invention.

EXAMPLE 3

APTES beads were made by adding 0.5 g 130 to 140 mesh silica gel to 200 uL APTES and 400 uL propanol. The beads were vortexed thoroughly for 10 seconds. 0.4 mL 1 N H2SO4 was added and vortexed for 10 seconds. The beads were incubated at 80° C. for 10 min and then cured at 110° C. for 1 hr.

1.67%, 2.5%, 5%, 6.67% and 10% SNP solutions were made by dissolving SNP in 25% DMSO in methanol. Solutions were stored in light proof containers.

The beads were packed into a 1/8" inside diameter Tygon tube that was 0.3" long. 0.5 ppm acetone in dry N2 was passed across the beads at 200 mL/min for 3 min. Then 90 uL of SNP solution was added to the beads and allowed to incubate for 3 min prior to imaging. A dark and easily visible color bar was present. The kinetics of the reaction were faster for higher concentrations of SNP. 10% SNP formed a precipitate after several days at standard temperature. The 6.67% SNP solution was stable for more than two weeks at room temperature, in the freezer and at 61 C.

A 150 uL 6.67% SNP solution was placed in a 5/16 inch outside diameter by 1/2 inch long black polyethylene tube and heat sealed on either side with 5/16 inch diameter mylar foil coated with polyethylene.

A 1/4 inch porous polyethylene disk is placed in one end of the cartridge and the ampoule containing the SNP solution is placed in after it. A 5/16 inch absorbent glass wool disk was placed on top of the ampoule and the top of the cartridge was sealed shut with a layer of mylar foil.

The cartridge was then flipped over and APTES beads (from the SNP Solution method example herein above) were placed into the middle portion of the cartridge. Another 1/4 inch porous polyethylene disk was used to trap the APTES beads in place. Then 30 to 60 mesh CaCl2 was added. Then, another 5/16 inch piece of glass wool was placed in the cartridge and the bottom was sealed shut with a layer of mylar foil.

The kinetics for SNP in solution are very rapid when SNP is at a concentration greater than 2% and when used with primary amines with a pH of between about 10 and 10.5.

SNP in solution has a larger gradient if acid is present in the developer solution or on the surface of the beads. This is because SNP is extracted from solution by positively-charged surfaces, created by proton coupling with primary amines. However, using a larger amount of solution can overcome these problems.

In accordance with yet another aspect of the invention, a method is provided for analyzing acetone in breath. The method comprises preparing a surface upon which is disposed a primary amine and a nitroprusside. The preparation comprises disposing the primary amine and the nitroprusside in an acidic environment. The method also comprises locating the surface upon which is disposed the primary amine and the nitroprusside within a cavity. The surface comprising the primary amine and the nitroprusside comprises a reference optical property. The surface preferably is in proximate contact with a solution. The method further comprises causing the breath to move into the cavity so that it contacts the primary amine and the nitroprusside to cause or facilitate a change in an optical property of the surface relative to the reference optical property. The method further comprises analyzing the breath for the presence of the acetone using the change in the optical property.

Figure 34:
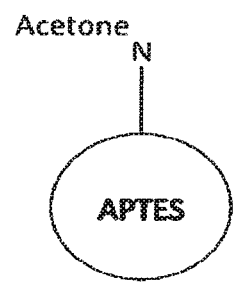
FIG. 34 shows a reaction scheme for analyzing acetone in breath.
Figure 34:
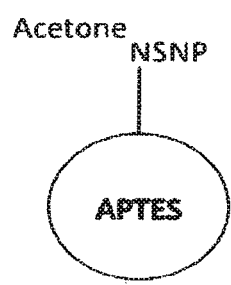
Figure 35:
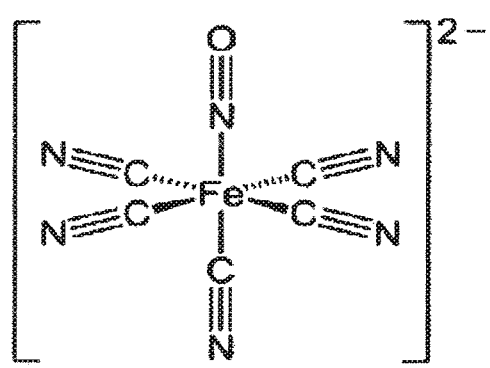
FIG. 35 shows a chemical structure of nitroprusside.

A preferred implementation of the method is provided in FIG. 34.

The present inventors have discovered that a truly stable SNP/primary amine group can be obtained by adjusting the pH to less than about 6 and even as low as 1. This results in a stability that exceeds that reported by Abbott, and that of urinalysis chemistry.

The urinalysis groups cannot use a pH of less than 7, because it makes the SNP non-reactive to acetone and other ketones. The present inventors have discovered that, by adding a base at least as strong as the primary amine to the developer solution at high concentration, superior stability can be achieved. This is believed to remove the protons, changing the pH and allowing the reaction to proceed.

The pH of the primary amine preferably is adjusted to between about 0 and 6, more preferably between about 0.5 and 4, and even more preferably between about 1 and 2. Nitroprusside is added to the acidic primary amines preferably between about 1 and 20%, more preferably between about 5 and 15%, and even more preferably between about 8 and 12%. The solution is then vacuum filtered and the beads are dried. In some embodiments, the beads are dried under vacuum. In other embodiments, they are dried on heat. In a preferred embodiment, they are dried at 110° C. for 30 min.

The developer solution comprises an organic solvent and a base. The solution preferably is between about 5 and 50%, more preferably between about 10 and 40%, and still more preferably between about 20 and 30% volume/volume composition with a base that has a pKb less than or equal to the pKb of the primary amine. The base preferably is aminopropyl triethoxysilane. More preferably, a base is used that is 1 or 2 units less than the pKb of the primary amine on the surface.

EXAMPLE 4

APTES beads were made by adding 0.5 g of 130 to 140 mesh silica gel to 200 uL of APTES in 800 uL of propanol and drying at 80° C. Following drying, the APTES beads were cured at 110° C.

0.5 g of the APTES beads thus made were added to 1.5 mL of IN HCl and 0.5 mL of H2O and incubated for 10 min. while rocking. 0.2 g of SNP was added and dissolved. The beads were filtered under vacuum, and then dried at 110° C. for 20 min.

The beads were packed into a ⅛" Inside diameter column that was 0.3" long. 0.5 ppm of acetone in dry N2 was passed across the beads at 200 mL/min for 3 min. Then 90 uL of developer solution (25% dimethylsulfoxide, 37.5% APTES in methanol) was added to the beads and they were allowed to incubate for 3 min. prior to imaging. A dark and easily visible color bar was observed.

This yielded a very stable method at 102° C. In this method, the primary amine was neutralized with acid (HCl, but less volatile acids are preferred, such as H2SO4) and coupled the SNP directly to it. Because the protons are already coupled to the primary amine, there is no diffusion over time that can lead to a change in performance. Also, because the nucleophiles are quenched and form a salt with the nitroprusside, the nitroprusside is stable over time. This method has shown stability for more than 96 hrs at 102° C. (i.e., estimated stability in excess of 1 yr at standard or room temperature).

Implementations of this method yield relatively fast kinetics. Kinetics of reaction are driven by the concentration of Schiff base, the concentration of fully-solubilized nitroprusside, the diffusion time for nitroprusside, and the pH. The kinetics are advanced by the relatively high concentration of primary amines and nitroprusside, the fact that diffusion is negligible with nitroprusside coupled directly to the primary amines, and with the proper reaction conditions.

The method can present problems, however, with gradient formation. In order to get the primary amines to react with acetone/SNP to form the color change, the pH must be greatly increased. This requires the use of strong bases that can strip the proton away from the primary amine. The strong bases are then quenched from the protons they strip from the surface, creating a pH gradient and a charge gradient along the column. The longer the column relative to the diffusion time of the developer solution, the more of a problem this is. Further, the charge gradient causes a larger amount of nitroprusside to follow the positive charges, creating a color gradient. The very high pH at the beginning of the column where the developer solution first comes in contact is sufficient to completely bleach the signal.

This problem can be addressed by using a short column, a pressurized method to add the developer solution, or a method to introduce the developer solution throughout the length of the column simultaneously.

It will be appreciated that the invention is not limited to the specific embodiments and method implementations described herein. The description herein has largely been explained with respect to human patients or subjects, but this is not necessarily limiting. The principles of the invention also may be applied in veterinary applications.

Having now described the invention and preferred embodiments and methods of it, it will be appreciated that the invention in its broader aspects is not limited to the specific details, representative devices and methods, and illustrative examples shown and described herein above. As noted herein above, the invention according to its various aspects is particularly pointed out and distinctly claimed in the attached claims read in view of this specification, and appropriate equivalents.

We claim:

1. A method for sensing acetone in breath, the method comprising:
   providing a cartridge comprising:
      a reactant in a reaction zone, wherein the reactant comprises an amine disposed on a solid surface, and
      a nitroprusside in a reaction zone, the nitroprusside disposed on a solid surface,
      wherein the reaction zone has an optical characteristic that is at a reference level;
   causing a breath sample to be passed through the cartridge such that the acetone in the breath sample reacts with the reactant to form a reaction product, wherein the reaction product is configured to react with the nitroprusside,
   resulting in a change in the optical characteristic of the reaction zone relative to the reference level; and
   measuring the change in the optical characteristic of the reaction zone, said change reflective of a concentration of acetone in the breath sample.

2. The method of claim 1, wherein causing the breath sample to be passed through the cartridge comprises pumping the breath sample through the cartridge.

3. The method of claim 1, wherein the solid surface comprises a silica gel.

4. The method of claim 1, wherein the solid surface comprises surfaces of a plurality of silica gel beads.

5. The method of claim 4, wherein the silica gel beads have a size distribution between 270 and 100 mesh.

6. The method of claim 1, further comprising maintaining the reactant in an alkaline environment.

7. The method of claim 1, wherein the amine is quenched with a non-volatile acid.

8. The method of claim 1, wherein the amine is quenched with sulfuric acid.

9. The method of claim 1, further comprising removing humidity from the breath sample before causing the breath sample to pass through the reaction zone of the cartridge.

10. The method of claim 9, wherein removing humidity from the breath sample comprises causing the breath sample to pass through a desiccant.

11. The method of claim 1, wherein the amine and the nitroprusside are disposed on the same solid surface together.

12. The method of claim 1, wherein the amine is a primary amine.

13. The method of claim 1, wherein the amine is aminopropyltriethoxysilane (APTES).

14. The method of claim 1, wherein the nitroprusside is sodium nitroprusside.

15. A breath analysis system, comprising:
   a cartridge having a reaction zone containing a reactant, the reaction zone forming part of a flow path through the cartridge, the reactant comprising an amine disposed on a solid surface, the reaction zone further comprising a nitroprusside disposed on a solid surface, the reaction zone having an optical characteristic that is at a reference level, wherein the cartridge is configured such that, when a breath sample is passed along the flow path, acetone in the breath sample reacts with the reactant to form a reaction product, the reaction product configured to react with the nitroprusside resulting in a change in the optical characteristic of the reaction zone relative to the reference level; and an optical sensor positioned to measure the change in the optical characteristic of the reaction zone, said change reflective of a concentration level of acetone in the breath sample.

16. The breath analysis system of claim 15, wherein the solid surface comprises a silica gel.

17. The breath analysis system of claim 15, wherein the solid surface comprises surfaces of a plurality of silica gel beads.

18. The breath analysis system of claim 17, wherein the silica gel beads have a size distribution between 270 and 100 mesh.

19. The breath analysis system of claim 15, wherein the amine is quenched with a non-volatile acid.

20. The breath analysis system of claim 15, wherein the amine is quenched with sulfuric acid.

21. The breath analysis system of claim 15, further comprising a desiccant for removing humidity from the breath sample.

22. The breath analysis system of claim 21, wherein the desiccant is selected from a group consisting of: ascarite, sodium hydroxide and calcium chloride.

23. The breath analysis system of claim 15, wherein the amine and the nitroprusside are disposed on the same solid surface together.

24. The breath analysis system of claim 15, wherein the nitroprusside is disposed on the solid surface without formation of a chemical bond.

25. The breath analysis system of claim 15, wherein the amine is a primary amine.

26. The breath analysis system of claim 15, wherein the amine is aminopropyltriethoxysilane (APTES).

27. The breath analysis system of claim 15, wherein the nitroprusside is sodium nitroprusside.

* * * * *